(12) United States Patent
Li et al.

(10) Patent No.: US 11,718,674 B2
(45) Date of Patent: Aug. 8, 2023

(54) ANTIBODIES BINDING PD-L1 AND USES THEREOF

(71) Applicant: Beijing Mabworks Biotech Co. Ltd., Beijing (CN)

(72) Inventors: Jiangmei Li, Beijing (CN); Wenqi Hu, Beijing (CN); Feng Li, Beijing (CN)

(73) Assignee: BEIJING MABWORKS BIOTECH CO., LTD., Beijing (CN)

( * ) Notice: Subject to any disclaimer, the term of this patent is extended or adjusted under 35 U.S.C. 154(b) by 134 days.

(21) Appl. No.: 17/460,560

(22) Filed: Aug. 30, 2021

(65) Prior Publication Data
US 2022/0298244 A1    Sep. 22, 2022

(30) Foreign Application Priority Data
Mar. 16, 2021 (CN) .......................... 202110284404.8

(51) Int. Cl.
| | |
|---|---|
| *C07K 16/28* | (2006.01) |
| *A61P 35/00* | (2006.01) |
| *C12N 15/63* | (2006.01) |
| *A61K 39/00* | (2006.01) |

(52) U.S. Cl.
CPC .......... *C07K 16/2827* (2013.01); *A61P 35/00* (2018.01); *C12N 15/63* (2013.01); *A61K 2039/505* (2013.01)

(58) Field of Classification Search
CPC ............ C07K 16/2827; C07K 2317/24; C07K 2317/33; C07K 2317/70; C07K 2317/76; C07K 2317/92; C07K 2317/52; C07K 2317/56; C07K 2317/565; C07K 2317/73; A61P 35/00; A61P 31/00; C12N 15/63; A61K 2039/505; A61K 45/06
See application file for complete search history.

(56) References Cited

U.S. PATENT DOCUMENTS 10,336,824 B2 * 7/2019 West ...................... A61P 35/00

FOREIGN PATENT DOCUMENTS

| WO | WO-2008076560 A2 * | 6/2008 | ......... C07K 16/2818 |
| WO | WO-2015095766 A2 * | 6/2015 | ......... A61K 47/6851 |
| WO | WO-2022193561 A1 * | 9/2022 | ............. A61P 35/00 |

* cited by examiner

*Primary Examiner* — Adam Weidner
*Assistant Examiner* — John J Skoko, III
(74) *Attorney, Agent, or Firm* — Duane Morris LLP; Thomas J. Kowalski; Deborah L. Lu

(57) ABSTRACT

An isolated monoclonal antibody, or an antigen-binding portion thereof, that specifically binds human PD0-L1. A nucleic acid molecule encoding the antibody or antigen-binding portion thereof, an expression vector, a host cell and a method for expressing the antibody or antigen-binding portion thereof are also provided. The present disclosure further provides an immuneconjugate, a bispecific molecule, a chimeric antigen receptor, an oncolytic virus and a pharmaceutical composition comprising the antibody or antigen-binding portion thereof, as well as a treatment method using the antibody or antigen-binding portion thereof.

15 Claims, 6 Drawing Sheets

Specification includes a Sequence Listing.

```
                         SEQUENCE LISTING

<160> NUMBER OF SEQ ID NOS: 37

<210> SEQ ID NO 1
<211> LENGTH: 5
<212> TYPE: PRT
<213> ORGANISM: Artificial Sequence
<220> FEATURE:
<223> OTHER INFORMATION: VH-CDR1 of mouse, chimeric and humanized 3C2
      antibodies

<400> SEQUENCE: 1

Asp Tyr His Val Asn
1               5

<210> SEQ ID NO 2
<211> LENGTH: 17
<212> TYPE: PRT
<213> ORGANISM: Artificial Sequence
<220> FEATURE:
<223> OTHER INFORMATION: VH-CDR2 of mouse, chimeric and humanized 3C2
      antibodies

<400> SEQUENCE: 2

Trp Ile Phe Pro Gly Ser Gly Arg Thr Phe Tyr Thr Asp Lys Phe Lys
1               5                   10                  15

Gly

<210> SEQ ID NO 3
<211> LENGTH: 11
<212> TYPE: PRT
<213> ORGANISM: Artificial Sequence
<220> FEATURE:
<223> OTHER INFORMATION: VH-CDR3 of mouse, chimeric and humanized 3C2
      antibodies

<400> SEQUENCE: 3

Asp Tyr Gly Thr Ser Gly Tyr Gly Leu Val Tyr
1               5                   10

<210> SEQ ID NO 4
<211> LENGTH: 11
<212> TYPE: PRT
<213> ORGANISM: Artificial Sequence
<220> FEATURE:
<223> OTHER INFORMATION: VL-CDR1 of mouse, chimeric and humanized 3C2
      antibodies

<400> SEQUENCE: 4

Lys Ala Ser Asp Arg Ile Asn Asn Trp Leu Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: VL-CDR2 of mouse, chimeric and humanized 3C2
      antibodies

<400> SEQUENCE: 5

Gly Ala Thr Ser Leu Glu Thr
1               5
```

<210> SEQ ID NO 6
<211> LENGTH: 9
<212> TYPE: PRT
<213> ORGANISM: Artificial Sequence
<220> FEATURE:
<223> OTHER INFORMATION: VL-CDR3 of mouse, chimeric and humanized 3C2
      antibodies

<400> SEQUENCE: 6

Gln Gln Tyr Trp Asn Ile Pro Phe Thr
1               5

<210> SEQ ID NO 7
<211> LENGTH: 5
<212> TYPE: PRT
<213> ORGANISM: Artificial Sequence
<220> FEATURE:
<223> OTHER INFORMATION: VH-CDR1 of mouse, chimeric and humanized 56E5
      antibodies

<400> SEQUENCE: 7

Ser Asp Tyr Trp Asn
1               5

<210> SEQ ID NO 8
<211> LENGTH: 16
<212> TYPE: PRT
<213> ORGANISM: Artificial Sequence
<220> FEATURE:
<223> OTHER INFORMATION: VH-CDR2 of mouse, chimeric and humanized 56E5
      antibodies

<400> SEQUENCE: 8

Tyr Ile Ser Tyr Thr Gly Ser Thr Tyr Tyr Asn Pro Ser Leu Lys Ser
1               5                   10                  15

<210> SEQ ID NO 9
<211> LENGTH: 11
<212> TYPE: PRT
<213> ORGANISM: Artificial Sequence
<220> FEATURE:
<223> OTHER INFORMATION: VH-CDR3 of mouse, chimeric and humanized 56E5
      antibodies

<400> SEQUENCE: 9

Tyr Arg Asp Trp Asp Val Arg Ala Met Asp Tyr
1               5                   10

<210> SEQ ID NO 10
<211> LENGTH: 17
<212> TYPE: PRT
<213> ORGANISM: Artificial Sequence
<220> FEATURE:
<223> OTHER INFORMATION: VL-CDR1 of mouse, chimeric and humanized 56E5
      antibodies

<400> SEQUENCE: 10

Lys Ser Ser Gln Ser Leu Leu Ile Ser Gly Asn Gln Lys Asn Phe Leu
1               5                   10                  15

Thr

<210> SEQ ID NO 11
<211> LENGTH: 7
<212> TYPE: PRT
<213> ORGANISM: Artificial Sequence
<220> FEATURE:
<223> OTHER INFORMATION: VL-CDR2 of mouse, chimeric and humanized 56E5 antibodies

<400> SEQUENCE: 11

Trp Ala Ser Thr Arg Glu Ser
1               5

<210> SEQ ID NO 12
<211> LENGTH: 9
<212> TYPE: PRT
<213> ORGANISM: Artificial Sequence
<220> FEATURE:
<223> OTHER INFORMATION: VL-CDR3 of mouse, chimeric and humanized 56E5
      antibodies

<400> SEQUENCE: 12

Gln Asn Asp Phe Gly Phe Pro Phe Thr
1               5

<210> SEQ ID NO 13
<211> LENGTH: 120
<212> TYPE: PRT
<213> ORGANISM: Artificial Sequence
<220> FEATURE:
<223> OTHER INFORMATION: VH of mouse and chimeric 3C2 antibodies

<400> SEQUENCE: 13

Gln Val Gln Leu Asn Gln Ser Gly Pro Glu Leu Met Lys Ala Gly Thr
1               5                   10                  15

Ser Val Lys Ile Ser Cys Lys Ala Ser Gly Tyr Ser Phe Thr Asp Tyr
                20                  25                  30

His Val Asn Trp Val Lys Gln Arg Pro Gly Gln Gly Leu Glu Trp Ile
            35                  40                  45

Gly Trp Ile Phe Pro Gly Ser Gly Arg Thr Tyr Thr Asp Lys Phe
        50                  55                  60

Lys Gly Lys Ala Thr Leu Thr Val Asp Leu Ser Phe Thr Thr Ala Tyr
65                  70                  75                  80

Ile Met Leu Asn Ser Leu Thr Ser Glu Asp Ser Ala Val Tyr Phe Cys
                85                  90                  95

Ala Thr Asp Tyr Gly Thr Ser Gly Tyr Gly Leu Val Tyr Trp Gly Gln
                100                 105                 110

Gly Thr Ser Val Thr Val Ser Ser
            115                 120

<210> SEQ ID NO 14
<211> LENGTH: 120
<212> TYPE: PRT
<213> ORGANISM: Artificial Sequence
<220> FEATURE:
<223> OTHER INFORMATION: VH of humanzed antibodies 3C2-VH2VL2,
      3C2-VH2VL3, and 3C2-VH2VL4

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

His Val Asn Trp Val Arg Gln Ala Pro Gly Gln Gly Leu Glu Trp Ile
            35                  40                  45

Gly Trp Ile Phe Pro Gly Ser Gly Arg Thr Tyr Thr Asp Lys Phe
        50                  55                  60

Lys Gly Arg Val Thr Leu Thr Val Asp Thr Ser Thr Ser Thr Val Tyr

```
                65                  70                  75                  80
Met Glu Leu Ser Ser Leu Thr Ser Glu Asp Thr Ala Val Tyr Tyr Cys
                        85                  90                  95

Ala Thr Asp Tyr Gly Thr Ser Gly Tyr Gly Leu Val Tyr Trp Gly Gln
                100                 105                 110

Gly Thr Thr Val Thr Val Ser Ser
        115                 120

<210> SEQ ID NO 15
<211> LENGTH: 120
<212> TYPE: PRT
<213> ORGANISM: Artificial Sequence
<220> FEATURE:
<223> OTHER INFORMATION: VH of humanized antibodies 3C2-VH3VL2,
      3C2-VH3VL3, and 3C2-VH3VL4

<400> SEQUENCE: 15

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

His Val Asn Trp Val Lys Gln Arg Pro Gly Gln Gly Leu Glu Trp Ile
            35                  40                  45

Gly Trp Ile Phe Pro Gly Ser Gly Arg Thr Phe Tyr Thr Asp Lys Phe
        50                  55                  60

Lys Gly Arg Val Thr Leu Thr Val Asp Thr Ser Ser Thr Val Tyr
65                  70                  75                  80

Met Glu Leu Ser Ser Leu Thr Ser Glu Asp Thr Ala Val Tyr Tyr Cys
                        85                  90                  95

Ala Thr Asp Tyr Gly Thr Ser Gly Tyr Gly Leu Val Tyr Trp Gly Gln
                100                 105                 110

Gly Thr Thr Val Thr Val Ser Ser
        115                 120

<210> SEQ ID NO 16
<211> LENGTH: 120
<212> TYPE: PRT
<213> ORGANISM: Artificial Sequence
<220> FEATURE:
<223> OTHER INFORMATION: VH of humanized antibodies 3C2-VH4VL2,
      3C2-VH4VL3, and 3C2-VH4VL4

<400> SEQUENCE: 16

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
                20                  25                  30

His Val Asn Trp Val Lys Gln Arg Pro Gly Gln Gly Leu Glu Trp Ile
            35                  40                  45

Gly Trp Ile Phe Pro Gly Ser Gly Arg Thr Phe Tyr Thr Asp Lys Phe
        50                  55                  60

Lys Gly Arg Val Thr Leu Thr Val Asp Thr Ser Thr Ser Thr Val Tyr
65                  70                  75                  80

Met Glu Leu Ser Ser Leu Thr Ser Glu Asp Thr Ala Val Tyr Phe Cys
                        85                  90                  95

Ala Thr Asp Tyr Gly Thr Ser Gly Tyr Gly Leu Val Tyr Trp Gly Gln
                100                 105                 110

Gly Thr Thr Val Thr Val Ser Ser
```

<210> SEQ ID NO 17
<211> LENGTH: 120
<212> TYPE: PRT
<213> ORGANISM: Artificial Sequence
<220> FEATURE:
<223> OTHER INFORMATION: VH of humanized antibodies 3C2-VH5VL2,
      3C2-VH5VL3, and 3C2-VH5VL4

<400> SEQUENCE: 17

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ser Phe Thr Asp Tyr
            20                  25                  30

His Val Asn Trp Val Lys Gln Arg Pro Gly Gln Gly Leu Glu Trp Ile
        35                  40                  45

Gly Trp Ile Phe Pro Gly Ser Gly Arg Thr Phe Tyr Thr Asp Lys Phe
    50                  55                  60

Lys Gly Lys Ala Thr Leu Thr Val Asp Thr Ser Thr Ser Thr Val Tyr
65                  70                  75                  80

Met Glu Leu Ser Ser Leu Thr Ser Glu Asp Thr Ala Val Tyr Phe Cys
                85                  90                  95

Ala Thr Asp Tyr Gly Thr Ser Gly Tyr Gly Leu Val Tyr Trp Gly Gln
            100                 105                 110

Gly Thr Thr Val Thr Val Ser Ser
        115                 120

<210> SEQ ID NO 18
<211> LENGTH: 120
<212> TYPE: PRT
<213> ORGANISM: Artificial Sequence
<220> FEATURE:
<223> OTHER INFORMATION: VH of humanized antibody 3C2-VH6VL5

<400> SEQUENCE: 18

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

His Val Asn Trp Val Arg Gln Ala Pro Gly Gln Gly Leu Glu Trp Ile
        35                  40                  45

Gly Trp Ile Phe Pro Gly Ser Gly Arg Thr Phe Tyr Thr Asp Lys Phe
    50                  55                  60

Lys Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Thr Asp Tyr Gly Thr Ser Gly Tyr Gly Leu Val Tyr Trp Gly Gln
            100                 105                 110

Gly Thr Thr Val Thr Val Ser Ser
        115                 120

<210> SEQ ID NO 19
<211> LENGTH: 119
<212> TYPE: PRT
<213> ORGANISM: Artificial Sequence
<220> FEATURE:
<223> OTHER INFORMATION: VH of mouse and chimeric 56E5 antibodies -continued

```
<400> SEQUENCE: 19

Glu Val Gln Leu Gln Glu Ser Gly Pro Gly Leu Ala Lys Pro Ser Gln
1               5                   10                  15

Thr Leu Ser Leu Thr Cys Ser Val Thr Gly Tyr Ser Ile Thr Ser Asp
            20                  25                  30

Tyr Trp Asn Trp Ile Arg Lys Phe Pro Gly Asn Lys Leu Glu Tyr Met
        35                  40                  45

Gly Tyr Ile Ser Tyr Thr Gly Ser Thr Tyr Tyr Asn Pro Ser Leu Lys
    50                  55                  60

Ser Arg Ile Ser Ile Thr Arg Asp Thr Ser Lys Asn Gln Tyr Tyr Leu
65                  70                  75                  80

Gln Leu Asn Ser Val Thr Thr Glu Asp Thr Ala Thr Tyr Tyr Cys Ala
                85                  90                  95

Arg Tyr Arg Asp Trp Asp Val Arg Ala Met Asp Tyr Trp Gly Gln Gly
            100                 105                 110

Thr Ser Val Thr Val Ser Ser
        115

<210> SEQ ID NO 20
<211> LENGTH: 119
<212> TYPE: PRT
<213> ORGANISM: Artificial Sequence
<220> FEATURE:
<223> OTHER INFORMATION: VH of humanized antibodies 56E5-VH2VL2,
      56E5-VH2VL3, and 56E5-VH2VL4

<400> SEQUENCE: 20

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Asp
            20                  25                  30

Tyr Trp Asn Trp Ile Arg Gln His Pro Gly Lys Gly Leu Glu Tyr Met
        35                  40                  45

Gly Tyr Ile Ser Tyr Thr Gly Ser Thr Tyr Tyr Asn Pro Ser Leu Lys
    50                  55                  60

Ser Arg Val Thr Ile Thr Val Asp Thr Ser Lys Asn Gln Phe Ser Leu
65                  70                  75                  80

Lys Leu Ser Ser Val Thr Thr Ala Asp Thr Ala Val Tyr Tyr Cys Ala
                85                  90                  95

Arg Tyr Arg Asp Trp Asp Val Arg Ala Met Asp Tyr Trp Gly Gln Gly
            100                 105                 110

Thr Thr Val Thr Val Ser Ser
        115

<210> SEQ ID NO 21
<211> LENGTH: 119
<212> TYPE: PRT
<213> ORGANISM: Artificial Sequence
<220> FEATURE:
<223> OTHER INFORMATION: VH of humanized antibodies 56E5-VH3VL2,
      56E5-VH3VL3 and 56E5-VH3VL4

<400> SEQUENCE: 21

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Asp
            20                  25                  30

Tyr Trp Asn Trp Ile Arg Gln His Pro Gly Asn Lys Leu Glu Tyr Met
```

```
            35                  40                  45
Gly Tyr Ile Ser Tyr Thr Gly Ser Thr Tyr Tyr Asn Pro Ser Leu Lys
        50                  55                  60

Ser Arg Val Thr Ile Thr Val Asp Thr Ser Lys Asn Gln Phe Ser Leu
65                  70                  75                  80

Lys Leu Ser Ser Val Thr Thr Ala Asp Thr Ala Val Tyr Tyr Cys Ala
                85                  90                  95

Arg Tyr Arg Asp Trp Asp Val Arg Ala Met Asp Tyr Trp Gly Gln Gly
            100                 105                 110

Thr Thr Val Thr Val Ser Ser
            115

<210> SEQ ID NO 22
<211> LENGTH: 119
<212> TYPE: PRT
<213> ORGANISM: Artificial Sequence
<220> FEATURE:
<223> OTHER INFORMATION: VH of humanized antibodies 56E5-VH4VL2,
      56E5-VH4VL3 and 56E5-VH4VL4

<400> SEQUENCE: 22

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Asp
            20                  25                  30

Tyr Trp Asn Trp Ile Arg Gln His Pro Gly Asn Lys Leu Glu Tyr Met
        35                  40                  45

Gly Tyr Ile Ser Tyr Thr Gly Ser Thr Tyr Tyr Asn Pro Ser Leu Lys
    50                  55                  60

Ser Arg Val Thr Ile Thr Arg Asp Thr Ser Lys Asn Gln Phe Ser Leu
65                  70                  75                  80

Lys Leu Ser Ser Val Thr Thr Ala Asp Thr Ala Val Tyr Tyr Cys Ala
                85                  90                  95

Arg Tyr Arg Asp Trp Asp Val Arg Ala Met Asp Tyr Trp Gly Gln Gly
            100                 105                 110

Thr Thr Val Thr Val Ser Ser
            115

<210> SEQ ID NO 23
<211> LENGTH: 119
<212> TYPE: PRT
<213> ORGANISM: Artificial Sequence
<220> FEATURE:
<223> OTHER INFORMATION: VH of humanized antibodies 56E5-VH5VL2,
      56E5-VH5VL3 and 56E5-VH5VL4

<400> SEQUENCE: 23

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Ser Asp
            20                  25                  30

Tyr Trp Asn Trp Ile Arg Gln His Pro Gly Asn Lys Leu Glu Tyr Met
        35                  40                  45

Gly Tyr Ile Ser Tyr Thr Gly Ser Thr Tyr Tyr Asn Pro Ser Leu Lys
    50                  55                  60

Ser Arg Ile Ser Ile Thr Arg Asp Thr Ser Lys Asn Gln Phe Ser Leu
65                  70                  75                  80

Lys Leu Ser Ser Val Thr Thr Ala Asp Thr Ala Val Tyr Tyr Cys Ala
```

85                  90                  95

Arg Tyr Arg Asp Trp Asp Val Arg Ala Met Asp Tyr Trp Gly Gln Gly
            100                 105                 110

Thr Thr Val Thr Val Ser Ser
        115

<210> SEQ ID NO 24
<211> LENGTH: 107
<212> TYPE: PRT
<213> ORGANISM: Artificial Sequence
<220> FEATURE:
<223> OTHER INFORMATION: VL of mouse and chimeric 3C2 antibodies

<400> SEQUENCE: 24

Asp Ile Gln Met Thr Gln Ser Ser Ser Tyr Leu Ser Val Ser Leu Gly
1               5                   10                  15

Gly Arg Val Thr Ile Ser Cys Lys Ala Ser Asp Arg Ile Asn Asn Trp
            20                  25                  30

Leu Ala Trp Tyr Gln Gln Lys Pro Gly Asn Ala Pro Arg Leu Leu Ile
            35                  40                  45

Ser Gly Ala Thr Ser Leu Glu Thr Gly Val Pro Ser Arg Phe Ser Gly
    50                  55                  60

Ser Gly Ser Gly Lys Asp Tyr Thr Leu Ser Ile Thr Ser Leu Gln Thr
65                  70                  75                  80

Glu Asp Val Ala Val Tyr Tyr Cys Gln Gln Tyr Trp Asn Ile Pro Phe
                85                  90                  95

Thr Phe Gly Ser Gly Thr Lys Leu Glu Ile Lys
            100                 105

<210> SEQ ID NO 25
<211> LENGTH: 107
<212> TYPE: PRT
<213> ORGANISM: Artificial Sequence
<220> FEATURE:
<223> OTHER INFORMATION: VL of humanized antibodies 3C2-VH2VL2,
      3C2-VH3VL2, 3C2-VH4VL2 and 3C2-VH5VL2

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp Arg Ile Asn Asn Trp
            20                  25                  30

Leu Ala Trp Tyr Gln Gln Lys Pro Gly Lys Ala Pro Arg Leu Leu Ile
            35                  40                  45

Ser Gly Ala Thr Ser Leu Glu Thr Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Trp Asn Ile Pro Phe
                85                  90                  95

Thr Phe Gly Gln Gly Thr Lys Val Glu Ile Lys
            100                 105

<210> SEQ ID NO 26
<211> LENGTH: 107
<212> TYPE: PRT
<213> ORGANISM: Artificial Sequence
<220> FEATURE:
<223> OTHER INFORMATION: VL of humanized antibodies 3C2-VH2VL3,
      3C2-VH3VL3, 3C2-VH4VL3 and 3C2-VH5VL3

```
<400> SEQUENCE: 26

Asp Ile Gln Met Thr Gln Ser Pro Ser Ser Leu Ser Ala Ser Val Gly
1               5                   10                  15

Asp Arg Val Thr Ile Ser Cys Lys Ala Ser Asp Arg Ile Asn Asn Trp
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Thr Tyr Tyr Cys Gln Gln Tyr Trp Asn Ile Pro Phe
                85                  90                  95

Thr Phe Gly Gln Gly Thr Lys Val Glu Ile Lys
            100                 105

<210> SEQ ID NO 27
<211> LENGTH: 107
<212> TYPE: PRT
<213> ORGANISM: Artificial Sequence
<220> FEATURE:
<223> OTHER INFORMATION: VL of humanized antibodies 3C2-VH2VL4,
      3C2-VH3VL4, 3C2-VH4VL4 and 3C2-VH5VL4

<400> SEQUENCE: 27

Asp Ile Gln Met Thr Gln Ser Pro Ser Ser Leu Ser Ala Ser Val Gly
1               5                   10                  15

Asp Arg Val Thr Ile Ser Cys Lys Ala Ser Asp Arg Ile Asn Asn Trp
            20                  25                  30

Leu Ala Trp Tyr Gln Gln Lys Pro Gly Asn Ala Pro Arg Leu Leu Ile
        35                  40                  45

Ser Gly Ala Thr Ser Leu Glu Thr Gly Val Pro Ser Arg Phe Ser Gly
    50                  55                  60

Ser Gly Ser Gly Thr Asp Tyr Thr Phe Thr Ile Ser Ser Leu Gln Pro
65                  70                  75                  80

Glu Asp Ile Ala Val Tyr Tyr Cys Gln Gln Tyr Trp Asn Ile Pro Phe
                85                  90                  95

Thr Phe Gly Gln Gly Thr Lys Val Glu Ile Lys
            100                 105

<210> SEQ ID NO 28
<211> LENGTH: 107
<212> TYPE: PRT
<213> ORGANISM: Artificial Sequence
<220> FEATURE:
<223> OTHER INFORMATION: VL of humanized antibody 3C2-VH6VL5

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Lys Ala Ser Asp Arg Ile Asn Asn Trp
            20                  25                  30

Leu Ala Trp Tyr Gln Gln Lys Pro Gly Lys Ala Pro Lys Leu Leu Ile
        35                  40                  45

Ser Gly Ala Thr Ser Leu Glu Thr Gly Val Pro Ser Arg Phe Ser Gly
    50                  55                  60

Ser Gly Ser Gly Thr Asp Phe Thr Leu Thr Ile Ser Ser Leu Gln Pro
```

```
                65                  70                  75                  80
Glu Asp Ile Ala Thr Tyr Tyr Cys Gln Gln Tyr Trp Asn Ile Pro Phe
                    85                  90                  95

Thr Phe Gly Gln Gly Thr Lys Val Glu Ile Lys
                100                 105
```

<210> SEQ ID NO 29
<211> LENGTH: 113
<212> TYPE: PRT
<213> ORGANISM: Artificial Sequence
<220> FEATURE:
<223> OTHER INFORMATION: VL of mouse and chimeric 56E5 antibodies

<400> SEQUENCE: 29

```
Asp Ile Val Met Thr Gln Ser Pro Ser Ser Leu Thr Val Thr Ala Gly
1               5                   10                  15

Glu Lys Val Thr Met Asn Cys Lys Ser Ser Gln Ser Leu Leu Ile Ser
                20                  25                  30

Gly Asn Gln Lys Asn Phe Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys Gln Asn
                85                  90                  95

Asp Phe Gly Phe Pro Phe Thr Phe Gly Ser Gly Thr Lys Leu Glu Ile
                100                 105                 110

Lys
```

<210> SEQ ID NO 30
<211> LENGTH: 113
<212> TYPE: PRT
<213> ORGANISM: Artificial Sequence
<220> FEATURE:
<223> OTHER INFORMATION: VL of humanized antibodies 56E5-VH2VL2,
      56E5-VH3VL2, 56E5-VH4VL2 and 56E5-VH5VL2

<400> SEQUENCE: 30

```
Asp Ile Val Met Thr Gln Ser Pro Asp Ser Leu Ala Val Ser Leu Gly
1               5                   10                  15

Glu Arg Ala Thr Met Asn Cys Lys Ser Ser Gln Ser Leu Leu Ile Ser
                20                  25                  30

Gly Asn Gln Lys Asn Phe Leu Thr Trp Tyr Gln Gln Lys Pro Gly Gln
            35                  40                  45

Pro Pro Lys Leu Leu Ile Tyr Trp Ala Ser Thr Arg Glu Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Phe Gly Phe Pro Phe Thr Phe Gly Gln Gly Thr Lys Val Glu Ile
                100                 105                 110

Lys
```

<210> SEQ ID NO 31
<211> LENGTH: 113
<212> TYPE: PRT

```
<213> ORGANISM: Artificial Sequence
<220> FEATURE:
<223> OTHER INFORMATION: VL of humanized antibodies 56E5-VH2VL3,
      56E5-VH3VL3, 56E5-VH4VL3 and 56E5-VH5VL3

<400> SEQUENCE: 31

Asp Ile Val Met Thr Gln Ser Pro Asp Ser Leu Ala Val Ser Leu Gly
1               5                   10                  15

Glu Lys Val Thr Met Asn Cys Lys Ser Ser Gln Ser Leu Leu Ile Ser
            20                  25                  30

Gly Asn Gln Lys Asn Phe Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asp Phe Gly Phe Pro Phe Thr Phe Gly Gln Gly Thr Lys Val Glu Ile
            100                 105                 110

Lys

<210> SEQ ID NO 32
<211> LENGTH: 113
<212> TYPE: PRT
<213> ORGANISM: Artificial Sequence
<220> FEATURE:
<223> OTHER INFORMATION: VL of humanized antibodies 56E5-VH2VL4,
      56E5-VH3VL4, 56E5-VH4VL4 and 56E5-VH5VL4

<400> SEQUENCE: 32

Asp Ile Val Met Thr Gln Ser Pro Asp Ser Leu Ala Val Ser Leu Gly
1               5                   10                  15

Glu Lys Val Thr Met Asn Cys Lys Ser Ser Gln Ser Leu Leu Ile Ser
            20                  25                  30

Gly Asn Gln Lys Asn Phe Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Leu Ala Val Tyr Tyr Cys Gln Asn
                85                  90                  95

Asp Phe Gly Phe Pro Phe Thr Phe Gly Gln Gly Thr Lys Val Glu Ile
            100                 105                 110

Lys

<210> SEQ ID NO 33
<211> LENGTH: 330
<212> TYPE: PRT
<213> ORGANISM: Artificial Sequence
<220> FEATURE:
<223> OTHER INFORMATION: Human IgG1 constant region (N297A)

<400> SEQUENCE: 33

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Ala Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 34
<211> LENGTH: 107
<212> TYPE: PRT
<213> ORGANISM: Artificial Sequence
<220> FEATURE:
<223> OTHER INFORMATION: Human kappa constant region

<400> SEQUENCE: 34

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

```
Thr Tyr Ser Leu Ser Ser Thr Leu Thr Leu Ser Lys Ala Asp Tyr Glu
 65                  70                  75                  80

Lys His Lys Val Tyr Ala Cys Glu Val Thr His Gln Gly Leu Ser Ser
                 85                  90                  95

Pro Val Thr Lys Ser Phe Asn Arg Gly Glu Cys
            100                 105

<210> SEQ ID NO 35
<211> LENGTH: 290
<212> TYPE: PRT
<213> ORGANISM: Homo sapiens

<400> SEQUENCE: 35

Met Arg Ile Phe Ala Val Phe Ile Phe Met Thr Tyr Trp His Leu Leu
 1               5                  10                  15

Asn Ala Phe Thr Val Thr Val Pro Lys Asp Leu Tyr Val Val Glu Tyr
                 20                  25                  30

Gly Ser Asn Met Thr Ile Glu Cys Lys Phe Pro Val Glu Lys Gln Leu
                 35                  40                  45

Asp Leu Ala Ala Leu Ile Val Tyr Trp Glu Met Glu Asp Lys Asn Ile
 50                  55                  60

Ile Gln Phe Val His Gly Glu Glu Asp Leu Lys Val Gln His Ser Ser
 65                  70                  75                  80

Tyr Arg Gln Arg Ala Arg Leu Leu Lys Asp Gln Leu Ser Leu Gly Asn
                 85                  90                  95

Ala Ala Leu Gln Ile Thr Asp Val Lys Leu Gln Asp Ala Gly Val Tyr
                100                 105                 110

Arg Cys Met Ile Ser Tyr Gly Gly Ala Asp Tyr Lys Arg Ile Thr Val
                115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Phe Asn
                180                 185                 190

Val Thr Ser Thr Leu Arg Ile Asn Thr Thr Asn Glu Ile Phe Tyr
                195                 200                 205

Cys Thr Phe Arg Arg Leu Asp Pro Glu Glu Asn His Thr Ala Glu Leu
210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
                260                 265                 270

Gly Ile Gln Asp Thr Asn Ser Lys Lys Gln Ser Asp Thr His Leu Glu
            275                 280                 285

Glu Thr
    290

<210> SEQ ID NO 36
<211> LENGTH: 290
<212> TYPE: PRT
```

<213> ORGANISM: Macaca fascicularis

<400> SEQUENCE: 36

Met Arg Ile Phe Ala Val Phe Ile Phe Thr Ile Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Thr Ser Leu Ile Val Tyr Trp Glu Met Glu Asp Lys Asn Ile
50                  55                  60

Ile Gln Phe Val His Gly Glu Glu Asp Leu Lys Val Gln His Ser Asn
65                  70                  75                  80

Tyr Arg Gln Arg Ala Gln Leu Leu Lys Asp Gln Leu Ser Leu Gly Asn
                85                  90                  95

Ala Ala Leu Arg Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
                165                 170                 175

Gly Lys Thr Thr Thr Thr Asn Ser Lys Arg Glu Glu Lys Leu Leu Asn
            180                 185                 190

Val Thr Ser Thr Leu Arg Ile Asn Thr Thr Ala Asn Glu Ile Phe Tyr
        195                 200                 205

Cys Ile Phe Arg Arg Leu Asp Pro Glu Glu Asn His Thr Ala Glu Leu
210                 215                 220

Val Ile Pro Glu Leu Pro Leu Ala Leu Pro Pro Asn Glu Arg Thr His
225                 230                 235                 240

Leu Val Ile Leu Gly Ala Ile Phe Leu Leu Gly Val Ala Leu Thr
                245                 250                 255

Phe Ile Phe Tyr Leu Arg Lys Gly Arg Met Met Asp Met Lys Lys Cys
            260                 265                 270

Gly Ile Arg Val Thr Asn Ser Lys Lys Gln Arg Asp Thr Gln Leu Glu
        275                 280                 285

Glu Thr
    290

<210> SEQ ID NO 37
<211> LENGTH: 290
<212> TYPE: PRT
<213> ORGANISM: Mus musculus

<400> SEQUENCE: 37

Met Arg Ile Phe Ala Gly Ile Ile Phe Thr Ala Cys Cys His Leu Leu
1               5                   10                  15

Arg Ala Phe Thr Ile Thr Ala Pro Lys Asp Leu Tyr Val Val Glu Tyr
            20                  25                  30

Gly Ser Asn Val Thr Met Glu Cys Arg Phe Pro Val Glu Arg Glu Leu
        35                  40                  45

Asp Leu Leu Ala Leu Val Val Tyr Trp Glu Lys Glu Asp Glu Gln Val

```
                   50                  55                  60
Ile Gln Phe Val Ala Gly Glu Glu Asp Leu Lys Pro Gln His Ser Asn
 65                  70                  75                  80

Phe Arg Gly Arg Ala Ser Leu Pro Lys Asp Gln Leu Leu Lys Gly Asn
                 85                  90                  95

Ala Ala Leu Gln Ile Thr Asp Val Lys Leu Gln Asp Ala Gly Val Tyr
                100                 105                 110

Cys Cys Ile Ile Ser Tyr Gly Gly Ala Asp Tyr Lys Arg Ile Thr Leu
                115                 120                 125

Lys Val Asn Ala Pro Tyr Arg Lys Ile Asn Gln Arg Ile Ser Val Asp
                130                 135                 140

Pro Ala Thr Ser Glu His Glu Leu Ile Cys Gln Ala Glu Gly Tyr Pro
145                 150                 155                 160

Glu Ala Glu Val Ile Trp Thr Asn Ser Asp His Gln Pro Val Ser Gly
                165                 170                 175

Lys Arg Ser Val Thr Thr Ser Arg Thr Glu Gly Met Leu Leu Asn Val
                180                 185                 190

Thr Ser Ser Leu Arg Val Asn Ala Thr Ala Asn Asp Val Phe Tyr Cys
                195                 200                 205

Thr Phe Trp Arg Ser Gln Pro Gly Gln Asn His Thr Ala Glu Leu Ile
                210                 215                 220

Ile Pro Glu Leu Pro Ala Thr His Pro Pro Gln Asn Arg Thr His Trp
225                 230                 235                 240

Val Leu Leu Gly Ser Ile Leu Leu Phe Leu Ile Val Val Ser Thr Val
                245                 250                 255

Leu Leu Phe Leu Arg Lys Gln Val Arg Met Leu Asp Val Glu Lys Cys
                260                 265                 270

Gly Val Glu Asp Thr Ser Ser Lys Asn Arg Asn Asp Thr Gln Phe Glu
                275                 280                 285

Glu Thr
    290
```

US 11,718,674 B2

ANTIBODIES BINDING PD-L1 AND USES THEREOF

RELATED APPLICATIONS AND INCORPORATION BY REFERENCE

This application claims priority to Chinese Patent Application No. 202110284404.8 filed on Mar. 16, 2021.

The foregoing application, and all documents cited therein or during its prosecution ("appln cited documents") and all documents cited or referenced herein (including without limitation all literature documents, patents, published patent applications cited herein) ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference. Any Genbank sequences mentioned in this disclosure are incorporated by reference with the Genbank sequence to be that of the earliest effective filing date of this disclosure.

Citation or identification of any document in this application is not an admission that such document is available as prior art to the present disclosure.

SEQUENCE STATEMENT

The instant application contains a Sequence Listing, which has been submitted electronically and is hereby incorporated by reference in its entirety. Said ASCII copy, is named 55556_00065SL.txt and is 37 kb in size.

FIELD OF THE INVENTION

The disclosure relates to an antibody or an antigen binding portion thereof specifically binding to human PD-L1, the preparation and use thereof, especially its use in treatment of diseases associated with PD-L1 signaling, such as cancers and infectious diseases.

BACKGROUND OF THE INVENTION

T cell-based immunity has evolved to recognize and destroy aberrant cells, including pathogen-infected cells and cancer cells. T cell activities are regulated by a series of co-stimulatory and co-inhibitory receptors as well as their ligands, known as immune checkpoints, which are critical for self-tolerance, preventing the immune system from attacking tissues indiscriminately.

Among the immune checkpoint pathways, the PD-L1/PD-1 signaling has revealed significant clinical benefits. PD-1, a type I transmembrane protein that negatively regulates immune responses, is mainly expressed on antigen-experienced memory T cells in peripheral tissues, and less commonly on B cells, activated monocytes, dendritic cells and natural killer cells (Keir M E et al., (2008) *Annu Rev Immunol.* 26:677-704; Ishida Y et al., (1992) *EMBO J.* 11(11):3887-3895). PD-L1 and PD-L2 are PD-1's ligands. PD-L1 is a type I transmembrane protein, consisting of two extracellular domains (the IgV- and IgC-like domains), a transmembrane domain, and an intracellular domain. It is constitutively expressed on antigen-presenting cells, T cells, B cells, monocytes, and epithelial cells, and is upregulated in many types of these cells at the presence of pro-inflammatory cytokines (Keir M E et al., (2008) supra; Chen J et al., (2016) *Ann Oncol.* 27(3):409-416). Studies have shown that PD-L1 induces IL-10 release and thus produces inhibitory effects on T cells (Dong H et al., (1999) *Nat Med.* 5(12):1365-1369). PD-L2 expression is almost restricted to antigen-presenting cells, and inducible expression can be found on e.g., dendritic cells and macrophages. Accumulating evidence showed PD-1 axis, when engaged with PD-L1, affects cytokine (e.g., IFN-γ, TNF-α, and IL-2) production to dampen T cell responses against normal cells/tissues (Keir M E et al., (2008) supra; Chen J et al., (2016) supra). The PD-1-PD-L1 interaction also inhibits secretion of cell survival factors, expression of transcription factors associated with effector cell functions, and lytic activities of activated B cells and NK cells (Terme M et al., (2011) *Cancer Res.* 71(16):5393-5399; Fanoni D et al., (2011) *Immunol Lett.* 134(2):157-160). PD-1 is also highly expressed on regulatory T cells (Treg), and may promote Treg activation and proliferation, further inhibiting the immune responses (Francisco L M et al., (2009) *J Exp Med.* 206(13):3015-3029).

PD-1 pathways may be utilized by tumor cells to evade hosts' immune surveillance. In specific, a large proportion of tumor-infiltrating lymphocytes (TILs) express a high level of PD-1s, while many tumor cells, including melanoma, ovarian cancer, lung cancer and renal cancer cells, constitutively express PD-1's ligands, especially PD-L1 (Dong H et al., (2002) *Nat Med.* 8(8):793-800; Kim J et al., (2005) *Am J Respir Cell Mol Biol.* 33(3):280-289; Lee S K et al., (2005) *J Dermatol Sci.* 40(2):95-103). PD-L1 is also expressed on myeloid cells, including a subset of macrophages and dendritic cells, in the microenvironment. Therefore, in the microenvironment, PD-L1-PD-1 interaction causes T cell dysfunction and exhaustion, IL-10 release, and reduced cytotoxicity against tumor cells by $CD8^+$ T cells, resulting in tumor cell growth (Zou W, Chen L. (2008) *Nat Rev Immunol.* 8(6):467-477; Sun Z et al., (2015) *Cancer Res.* 75(8):1635-1644). The immune responses may be further depressed by Tregs in the microenvironment (Francisco L M et al., (2009) supra), and PD-L1-CD80 heterodimers which dampen CD80-CTLA4 interaction (Butte M J et al., (2007) *Immunity.* 27(1):111-122; Paterson A M et al., (2011) *J Immunol.* 187(3):1097-1105).

PD-1/PD-L1 blockade by e.g., antibodies can induce durable tumor remissions in a number of cancers, including solid tumors and hematologic tumors. Till now, antibodies targeting the PD-L1-PD-1 axis are being evaluated in more than 1,000 clinical trials, for treating solid tumors, such as melanoma, non-small cell lung cancer (NSCLC), renal cell carcinoma (RCC), Hodgkin's lymphoma, bladder cancer, head and neck carcinoma, neuroendocrine tumor, microsatellite instable-high (MSI-H) and mismatch repair-deficient (dMMR) solid tumors, and hematologic tumors, such as mantle cell lymphoma, diffuse large B-cell lymphoma, and follicular lymphoma (Akinleye A, Rasool Z. (2019) *J Hematol Oncol.* 12(1):92; Chong Sun et. al. (2018) *Immunity* 20; 48(3):434-452). Three anti-PD-L1 antibodies have been approved by FDA, namely, Atezolizumab, Durvalumab, and Acelumab. Atezolizumab is a humanized IgG1 antibody that is able to block PD-L1-PD-1 and PD-L1-CD80 binding, its Fc region is designed to not induce antibody dependent cell mediated cytotoxicity (ADCC) so as to eliminate damage to $PD-L1^+$ T cells. Atezolizumab has shown clinical efficacy in solid and non-solid tumors, including NSCLC, melanoma, RCC, colorectal cancer, stomach cancer, head and neck squamous-cell carcinoma, and urothelial carcinoma. Similarly, the humanized antibody Durvalumab can block PD-L1 binding with PD-1 or CD80, and is designed to avoid ADCC against PD-L1+ T cells. It is efficacious in treating e.g., urothelial carcinoma and NSCLC. Avelumab, another humanized IgG1 antibody with Fc region not modified, can block PD-L1-PD-1 and PD-L1-CD80 interaction, induce ADCC against tumor cells, and has shown good clinical outcomes in treatment of Merkel-cell carcinoma, urothelial carcinoma, and three-negative breast cancer. Other anti-PD-L1 antibodies under clinical trials include Envafolimab and BMS-936559. The anti-PD-L1 antibodies may be used in combination with other antibodies, targeted agents, and/or chemotherapeutic agents, to better inhibit tumor growth.

However, not all patients are responsive to the anti-PD-1/PD-L1 therapies, despite of the therapies' wide-spectrum anti-tumor effects, and some patients reported encouraging initial responses, but eventually became resistant to the therapies. To find out the causes of such acquired resistance and to develop new agents/therapies would be extremely important. There remains a need for more anti-PD-L1 antibodies with different and/or improved pharmaceutical characteristics, e.g., antibodies with different binding affinities, different blocking capabilities on PD-1-PD-L1, and/or different binding epitopes.

The PD-L1/PD-1 blockade also showed good effects in clinical or pre-clinical studies of acute or chronic viral, bacterial, or parasite infections (Jubel J M et al., (2020) *Front Immunol.* 11:487). For example, in chronic infections by hepatitis B virus (HBV), hepatitis C virus (HCV), human immunodeficiency virus (HIV), or simian immunodeficiency virus (SIV), administration of anti-PD-L1 antibodies increased IFN-γ, IL-2 and TNFα release, functionally reversed T cell exhaustion, and ameliorated viremia. Thus, more anti-PD-L1 antibodies are also needed for infectious disease treatment.

SUMMARY OF THE INVENTION

The present disclosure provides an isolated monoclonal antibody, for example, a mouse, human, chimeric or humanized monoclonal antibody, that binds to PD-L1 (e.g., the human PD-L1, and monkey PD-L1), or an antigen-binding portion thereof. It has comparable or higher binding capability to human and monkey PD-L1 proteins, comparable blocking activity on PD-L1-PD-1 interaction, comparable or better T cell activation capability, and comparable or higher in vivo anti-tumor activity, as compared to prior art antibodies such as Atezolizumab.

The antibody or antigen-binding portion thereof of the disclosure can be used for a variety of applications, including detection of PD-L1 proteins and treatment of PD-L1 associated diseases.

Accordingly, in one aspect, the disclosure pertains to an isolated monoclonal antibody (e.g., a humanized antibody), or an antigen-binding portion thereof, that binds PD-L1, that may comprise i) a heavy chain variable region that may comprise a VH-CDR1 region, a VH-CDR2 region and a VH-CDR3 region, wherein the VH-CDR1 region, the VH-CDR2 region and the VH-CDR3 region may comprise amino acid sequences having at least 80%, 81%, 82%, 83%, 84%, 85%, 86%, 87%, 88%, 89%, 90%, 91%, 92%, 93%, 94%, 95%, 96%, 97%, 98%, or 99% identity to, or set forth in (1) SEQ ID NOs: 1, 2 and 3, respectively; or (2) SEQ ID NOs: 7, 8 and 9, respectively; and/or ii) a light chain variable region that may comprise a VL-CDR1 region, a VL-CDR2 region and a VL-CDR3 region, wherein the VL-CDR1 region, the VL-CDR2 region and the VL-CDR3 region may comprise amino acid sequences having at least 80%, 81%, 82%, 83%, 84%, 85%, 86%, 87%, 88%, 89%, 90%, 91%, 92%, 93%, 94%, 95%, 96%, 97%, 98%, or 99% identity to, or set forth in (1) SEQ ID NOs: 4, 5 and 6, respectively; or (2) SEQ ID NOs: 10, 11 and 12, respectively.

The isolated monoclonal antibody or antigen-binding portion thereof of the disclosure may comprise a heavy chain variable region and a light chain variable region, wherein the VH-CDR1 region, VH-CDR2 region, VH-CDR3 region, VL-CDR1 region, VL-CDR2 region and VL-CDR3 region may comprise amino acid sequences having at least 80%, 81%, 82%, 83%, 84%, 85%, 86%, 87%, 88%, 89%, 90%, 91%, 92%, 93%, 94%, 95%, 96%, 97%, 98%, or 99% identity to, or set forth in (1) SEQ ID NOs: 1, 2, 3, 4, 5 and 6, respectively; or (2) SEQ ID NOs: 7, 8, 9, 10, 11 and 12, respectively.

The heavy chain variable region of the disclosure may comprise an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% identity to, or set forth in any one of SEQ ID NOs: 13-23.

The light chain variable region of the disclosure may comprise an amino acid sequence having at least 80%, 81%, 82%, 83%, 84%, 85%, 86%, 87%, 88%, 89%, 90%, 91%, 92%, 93%, 94%, 95%, 96%, 97%, 98%, or 99% identity to, or set forth in any one of SEQ ID NOs: 24-32.

The isolated monoclonal antibody or antigen-binding portion thereof of the disclosure may comprise a heavy chain variable region and a light chain variable region which may comprise amino acid sequences having at least 80%, 81%, 82%, 83%, 84%, 85%, 86%, 87%, 88%, 89%, 90%, 91%, 92%, 93%, 94% 95%, 96%, 97%, 98%, or 99% identity to, or set forth in (1) SEQ ID NOs: 13 and 24, respectively; (2) SEQ ID NOs: 14 and 25, respectively; (3) SEQ ID NOs: 14 and 26, respectively; (4) SEQ ID NOs: 14 and 27, respectively; (5) SEQ ID NOs: 15 and 25, respectively; (6) SEQ ID NOs: 15 and 26, respectively; (7) SEQ ID NOs: 15 and 27, respectively; (8) SEQ ID NOs: 16 and 25, respectively; (9) SEQ ID NOs: 16 and 26, respectively; (10) SEQ ID NOs: 16 and 27, respectively; (11) SEQ ID NOs: 17 and 25, respectively; (12) SEQ ID NOs: 17 and 26, respectively; (13) SEQ ID NOs: 17 and 27, respectively; (14) SEQ ID NOs: 18 and 28, respectively; (15) SEQ ID NOs: 19 and 29, respectively; (16) SEQ ID NOs: 20 and 30, respectively; (17) SEQ ID NOs: 20 and 31, respectively; (18) SEQ ID NOs: 20 and 32, respectively; (19) SEQ ID NOs: 21 and 30, respectively; (20) SEQ ID NOs: 21 and 31, respectively; (21) SEQ ID NOs: 21 and 32, respectively; (22) SEQ ID NOs: 22 and 30, respectively; (23) SEQ ID NOs: 22 and 31, respectively; (24) SEQ ID NOs: 22 and 32, respectively; (25) SEQ ID NOs: 23 and 30, respectively; (26) SEQ ID NOs: 23 and 31, respectively; or (27) SEQ ID NOs: 23 and 32, respectively.

The isolated monoclonal antibody of the disclosure may comprise a heavy chain constant region and/or a light chain constant region. The heavy chain constant region may be an IgG1, IgG2, IgG3 or IgG4 heavy chain constant region, or a functional fragment thereof. The heavy chain constant region may be modified to induce decreased ADCC against PD-L1+ cells, or modified to not induce ADCC against PD-L1+ cells. For instance, the heavy chain constant region may be human IgG1 constant region with N297A mutation, having e.g., the amino acid sequence of SEQ ID NO: 33. The light chain constant region may be kappa light chain constant region such as human kappa light chain constant region, having e.g., the amino acid sequence of SEQ ID NO: 34. The N terminus of the heavy chain constant region is linked to the C terminus of the heavy chain variable region, and the N terminus of the light chain constant region is linked to the C terminus of the light chain variable region.

In certain embodiments, the antibody of the disclosure may comprise or consists of two heavy chains and two light chains connected by disulfide bonds, wherein each heavy chain comprises the heavy chain constant region, heavy chain variable region or CDR sequences mentioned above, and each light chain comprises the light chain constant region, light chain variable region or CDR sequences mentioned above. The antibody of the disclosure may be a full-length antibody, for example, of an IgG4, IgG1 or IgG2 isotype. The antibody or antigen binding portion thereof of the present disclosure in other embodiments may be a single chain antibody, or consists of antibody fragments, such as Fab or F(ab')2 fragments.

The exemplary antibody or antigen binding portion thereof of the disclosure is antagonistic, which binds to human/monkey PD-L1, blocks PD-L1-PD-1 interaction, induces T cell activation, and/or has in vivo anti-tumor effects.

The disclosure also provides an immuneconjugate comprising the antibody or the antigen binding portion thereof, linked to a therapeutic agent such as a cytotoxin or an anti-cancer agent. The disclosure also provides a bispecific molecule comprising the antibody or the antigen-binding portion thereof of the disclosure, linked to a second functional moiety (e.g., a second antibody) having a different binding specificity than the antibody or the antigen-binding portion thereof of the disclosure. In another aspect, the antibody or the antigen-binding portion thereof of the present disclosure can be made into part of a chimeric antigen receptor (CAR) or a T cell receptor (TCR). The disclosure further provides an immune cell with the CAR or TCR of the disclosure, such as a T cell and a NK cell. The antibody or antigen binding portion thereof of the disclosure can also be encoded by or used in conjunction with an oncolytic virus.

The disclosure further provides a nucleic acid molecule encoding the antibody or antigen-binding portion thereof of the disclosure, as well as an expression vector comprising such a nucleic acid molecule and a host cell comprising such an expression vector. A method for preparing the anti-PD-L1 antibody or antigen binding portion thereof using the host cell of the disclosure is provided, comprising steps of (i) expressing the antibody or antigen binding portion thereof in the host cell, and (ii) isolating the antibody or antigen binding portion thereof from the host cell or its cell culture.

The disclosure provides a composition comprising the antibody or antigen binding portion thereof, the immuneconjugate, the bispecific molecule, the immune cell, the oncolytic virus, the nucleic acid molecule, the expression vector, or the host cell of the disclosure, and a pharmaceutically acceptable carrier.

In another aspect, the disclosure provides a method for enhancing an immune response in a subject in need thereof, comprising administering to the subject a therapeutically effective amount of the composition of the disclosure. In some embodiments, the method comprises inducing T cell activation.

In another aspect, the disclosure provides a method for treating or alleviating cancer in a subject in need thereof, comprising administering to the subject a therapeutically effective amount of the composition of the disclosure. The cancer may be a solid cancer or a hematological cancer, including, but not limited to, melanoma, non-small cell lung cancer, renal cell carcinoma, Hodgkin lymphoma, bladder cancer, head and neck cancer, neuroendocrine tumor, mantle cell lymphoma, diffuse large B-cell lymphoma, and follicular lymphoma. In some embodiments, at least one additional anti-cancer antibody may be administered with the composition of the disclosure, such as an anti-PD-1 antibody, an anti-STAT3 antibody, an anti-ROR1 antibody, an anti-TIM-3 antibody, and/or an anti-CTLA-4 antibody. In certain embodiments, the composition of the disclosure may be administered with a cytokine (e.g., IL-2 and/or IL-21), or a costimulatory antibody (e.g., an anti-CD137 and/or anti-GITR antibody). In another embodiment, the composition of the disclosure may be administered with a chemotherapeutic agent, which may be a cytotoxic agent.

In another aspect, the disclosure provides a method for treating or alleviating an infectious disease in a subject in need thereof, comprising administering to the subject a therapeutically effective amount of the antibody or antigen binding portion thereof. The infectious disease may be a chronic viral, bacterial, fungal or mycoplasma infection, such as a chronic hepatitis B virus (HBV), hepatitis C virus (HCV), human immunodeficiency virus (HIV), or simian immunodeficiency virus (SIV) infection. In certain embodiments, at least one additional anti-infective agent may be administered with the antibody or antigen binding portion thereof of the disclosure, such as an anti-viral agent, an anti-bacterial agent, an anti-fungal agent, or an anti-mycoplasma agent.

Other features and advantages of the instant disclosure will be apparent from the following detailed description and examples, which should not be construed as limiting. The contents of all references, Genbank entries, patents and published patent applications cited throughout this application are expressly incorporated herein by reference.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. All rights to explicitly disclaim any embodiments that are the subject of any granted patent(s) of applicant in the lineage of this application or in any other lineage or in any prior filed application of any third party is explicitly reserved. Nothing herein is to be construed as a promise.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Figure 1:
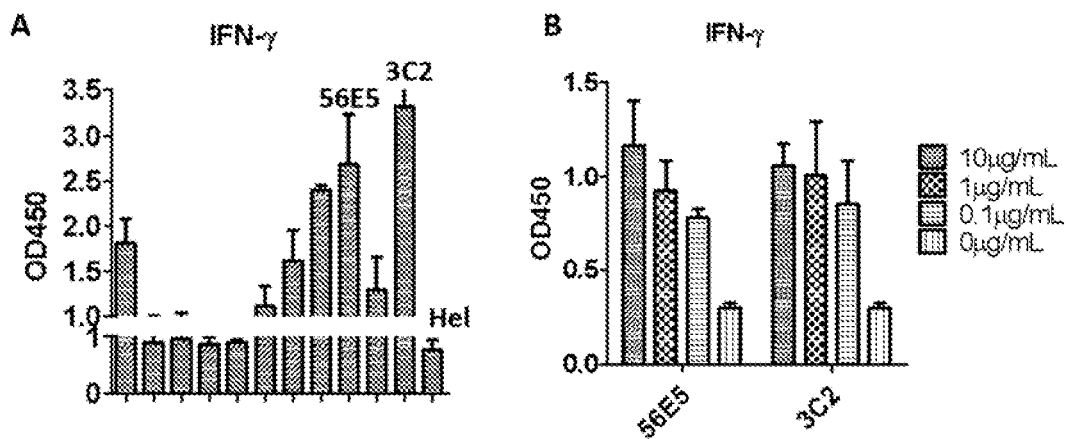
FIG. 1 shows the treatment of mouse anti-PD-L1 antibodies at 100 μg/ml (A) or at 0.1-10 μg/ml (B) increased IFN-γ secretion by T cells.

To ensure that the present disclosure may be more readily understood, certain terms are first defined. Additional definitions are set forth throughout the detailed description.

The term "PD-L1" refers to programmed death-ligand 1. The term "PD-L1" comprises variants, isoforms, homologs, orthologs and paralogs. For example, an antibody specific for a human PD-L1 protein may, in certain cases, cross-react with a PD-L1 protein from a species other than human, such as monkey. In other embodiments, an antibody specific for a human PD-L1 protein may be completely specific for the human PD-L1 protein and exhibit no cross-reactivity to other species or of other types, or may cross-react with PD-L1 from certain other species but not all other species.

The term "human PD-L1" refers to a PD-L1 protein having an amino acid sequence from a human, such as the amino acid sequence having a GenBank accession no. AAI13735.1 (Strausberg R. L. et al., (2002) Proc. Natl. Acad. Sci. U.S.A. 99(26): 16899-16903) or set forth in SEQ ID NO: 35. The term "monkey PD-L1" refers to a PD-L1 protein having an amino acid sequence from a monkey, such as the amino acid sequence having a NCBI accession no. XP_005581836.1 or set forth in SEQ ID NO: 36. The term "mouse PD-L1" refers to a PD-L1 protein having an amino acid sequence from a mouse, such as the amino acid sequence having a GenBank accession no. AAH66841.1 (Strausberg R. L. et al., (2002) supra) or set forth in SEQ ID NO: 37.

The term "antibody" as referred to herein includes whole antibodies of e.g., IgG, IgA, IgD, IgE and IgM, and any antigen binding fragment (i.e., "antigen-binding portion") or single chains thereof. Whole antibodies are glycoproteins comprising at least two heavy (H) chains and two light (L) chains inter-connected by disulfide bonds. Each heavy chain is comprised of a heavy chain variable region (abbreviated herein as $V_H$) and a heavy chain constant region. The heavy chain constant region is comprised of three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

The term "antigen-binding portion" of an antibody (or simply "antibody portion"), as used herein, refers to one or more fragments of an antibody that retain the ability to specifically bind to an antigen (e.g., a PD-L1 protein). It has been shown that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; (iv) a Fv fragment consisting of the $V_L$ and $V_H$ domains of a single arm of an antibody, (v) a dAb fragment (Ward et al., (1989) Nature 341:544-546), which consists of a $V_H$ domain; (vi) an isolated complementarity determining region (CDR); and (viii) a nanobody, a heavy chain variable region containing a single variable domain and two constant domains. Furthermore, although the two domains of the Fv fragment, $V_L$ and $V_H$, are coded by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al., (1988) Science 242:423-426; and Huston et al., (1988) Proc. Natl. Acad. Sci. USA 85:5879-5883). Such single chain antibodies are also intended to be encompassed within the term "antigen-binding portion" of an antibody. These antibody fragments are obtained using conventional techniques known to those with skill in the art, and the fragments are screened for utility in the same manner as are intact antibodies.

An "isolated antibody", as used herein, is intended to refer to an antibody that is substantially free of other antibodies having different antigenic specificities (e.g., an isolated antibody that specifically binds a PD-L1 protein is substantially free of antibodies that specifically bind antigens other than PD-L1 proteins). An isolated antibody that specifically binds a human PD-L1 protein may, however, have cross-reactivity to other antigens, such as PD-L1 proteins from other species. Moreover, an isolated antibody can be substantially free of other cellular material and/or chemicals.

The term "monoclonal antibody" as used herein refers to a population of substantially homogeneous antibodies, i.e., the individual antibodies comprising the population are identical except for possible naturally occurring mutations and/or post-translation modifications (e.g., isomerization, amidation) that may be present in minor amounts. Monoclonal antibodies are highly specific, being directed against a single antigenic site. In contrast to polyclonal antibody preparations which typically include different antibodies directed against different determinants (epitopes), the monoclonal antibodies are directed against a single determinant on the antigen.

The term "mouse antibody", as used herein, is intended to include antibodies having variable regions in which both the framework and CDR regions are derived from mouse germline immunoglobulin sequences. Furthermore, if the antibody contains a constant region, the constant region also is derived from mouse germline immunoglobulin sequences. The mouse antibodies of the disclosure can include amino acid residues not encoded by mouse germline immunoglobulin sequences (e.g., mutations introduced by random or site-specific mutagenesis in vitro or by somatic mutation in vivo). However, the term "mouse antibody", as used herein, is not intended to include antibodies in which CDR sequences derived from the germline of another mammalian species have been grafted onto mouse framework sequences.

The term "chimeric antibody" refers to an antibody made by combining genetic material from a nonhuman source with genetic material from a human being. Or more generally, a chimeric antibody is an antibody having genetic material from a certain species with genetic material from another species.

The term "humanized antibody", as used herein, refers to an antibody from non-human species whose protein sequences have been modified to increase similarity to antibody variants produced naturally in humans.

The phrases "an antibody recognizing an antigen" and "an antibody specific for an antigen" are used interchangeably herein with the term "an antibody which binds specifically to an antigen."

As used herein, an antibody that "specifically binds to human PD-L1" is intended to refer to an antibody that binds to human PD-L1 protein (and possibly a PD-L1 protein from one or more non-human species) but does not substantially bind to non-PD-L1 proteins. Preferably, the antibody binds to human PD-L1 protein with "high affinity", namely with a $K_D$ of $5.0 \times 10^{-8}$ M or less, more preferably $1.0 \times 10^{-9}$ M or less.

The term "does not substantially bind" to a protein or cells, as used herein, means does not bind or does not bind with a high affinity to the protein or cells, i.e. binds to the protein or cells with a $K_D$ of $1.0 \times 10^{-6}$ M or more, more preferably $1.0 \times 10^{-5}$ M or more, more preferably $1.0 \times 10^{-4}$ M or more, more preferably $1.0 \times 10^{-3}$ M or more, even more preferably $1.0 \times 10^{-2}$ M or more.

The term "high affinity" for an IgG antibody refers to an antibody having a $K_D$ of $1.0 \times 10^{-6}$ M or less, more preferably $5.0 \times 10^{-8}$ M or less, even more preferably $1.0 \times 10^{-8}$ M or less, even more preferably $5.0 \times 10^{-9}$ M or less and even more preferably $1.0 \times 10^{-9}$ M or less for a target antigen. However, "high affinity" binding can vary for other antibody isotypes. For example, "high affinity" binding for an IgM isotype refers to an antibody having a $K_D$ of $10^{-6}$ M or less, more preferably $10^{-7}$ M or less, even more preferably $10^{-8}$ M or less.

The term "$K_{assoc}$" or "$K_a$", as used herein, is intended to refer to the association rate of a particular antibody-antigen interaction, whereas the term "$K_{dis}$" or "$K_d$", as used herein, is intended to refer to the dissociation rate of a particular antibody-antigen interaction. The term "$K_D$", as used herein, is intended to refer to the dissociation constant, which is obtained from the ratio of $K_d$ to $K_a$ (i.e., $K_d/K_a$) and is expressed as a molar concentration (M). $K_D$ values for antibodies can be determined using methods well established in the art. A preferred method for determining the $K_D$ of an antibody is by using surface plasmon resonance, preferably using a biosensor system such as a Biacore™ system.

The term "$EC_{50}$", also known as half maximal effective concentration, refers to the concentration of an antibody which induces a response halfway between the baseline and maximum after a specified exposure time.

The term "antibody dependent cellular cytotoxicity", "antibody dependent cell-mediated cytotoxicity" or "ADCC" refers to a mechanism of cell-mediated immune defense whereby an effector cell of the immune system actively lyses a target cell bound by antibodies.

The term "subject" includes any human or nonhuman animal. The term "nonhuman animal" includes all vertebrates, e.g., mammals and non-mammals, such as non-human primates, sheep, dogs, cats, cows, horses, chickens, amphibians, and reptiles, although mammals are preferred, such as non-human primates, sheep, dogs, cats, cows and horses.

The term "antagonistic PD-L1 antibody" or "antagonistic anti-PD-L1 antibody" refers to an anti-PD-L1 antibody that binds to PD-L1 and blocks PD-L1 signaling induced by PD-L1's interaction with its ligands such as PD-1. The antagonistic anti-PD-L1 antibody may promote T cell activation and cytokine release, enhance immunity, and thus can be used to treat e.g., cancers and chronic infections.

The term "therapeutically effective amount" means an amount of the antibody or antigen binding portion thereof of the present disclosure sufficient to prevent or ameliorate the symptoms associated with a disease or condition (such as a cancer) and/or lessen the severity of the disease or condition. A therapeutically effective amount is understood to be in context of the condition being treated, where the actual effective amount is readily discerned by those of skill in the art.

Various aspects of the disclosure are described in further detail in the following subsections.

The exemplary antibodies, or antigen binding portions thereof, of the disclosure specifically bind to human and monkey PD-L1 proteins with high binding capabilities that are similar to or higher than those of prior art anti-PD-L1 antibodies such as Atezolizumab. The antibodies or antigen binding portions thereof of the disclosure may block PD-L1-PD-1 binding or interaction, and the blocking activities are comparable to those of prior art anti-PD-L1 antibodies such as Atezolizumab.

More importantly, the antibodies or antigen binding portions thereof of the disclosure have comparable, if not higher, T cell activating capabilities and in vivo anti-tumor activities, compared to prior art anti-PD-L1 antibodies such as Atezolizumab.

Preferred antibodies or antigen binding portions thereof of the disclosure are monoclonal. Additionally, the antibodies or antigen binding portions thereof can be, for example, mouse, chimeric or humanized.

The exemplary antibodies or antigen binding portions thereof of the disclosure are structurally and chemically characterized below. The sequence ID numbers of their heavy chain and light chain variable regions and CDRs are summarized in Table 1, some antibodies or antigen binding portions thereof share the same heavy/light chain variable regions.

Accordingly, in one embodiment, an antibody of the disclosure, or an antigen binding portion thereof, comprises:
(a) a heavy chain variable region comprising an amino acid sequence listed above in Table 1; and
(b) a light chain variable region comprising an amino acid sequence listed above in Table 1, or the $V_L$ of another anti-PD-L1 antibody, wherein the antibody specifically binds human PD-L1.

TABLE 1

Amino acid sequence ID NOs. of heavy/light chain variable regions and CDRs

| mAb no. | HV-CDR1 | HV-CDR2 | HV-CDR3 | HV | LV-CDR1 | LV-CDR2 | LV-CDR3 | LV |
|---|---|---|---|---|---|---|---|---|
| Mouse and chimeric 3C2 | 1 | 2 | 3 | 13 | 4 | 5 | 6 | 24 |
| 3C2-VH2VL2 | 1 | 2 | 3 | 14 | 4 | 5 | 6 | 25 |
| 3C2-VH2VL3 | 1 | 2 | 3 | 14 | 4 | 5 | 6 | 26 |
| 3C2-VH2VL4 | 1 | 2 | 3 | 14 | 4 | 5 | 6 | 27 |
| 3C2-VH3VL2 | 1 | 2 | 3 | 15 | 4 | 5 | 6 | 25 |
| 3C2-VH3VL3 | 1 | 2 | 3 | 15 | 4 | 5 | 6 | 26 |
| 3C2-VH3VL4 | 1 | 2 | 3 | 15 | 4 | 5 | 6 | 27 |
| 3C2-VH4VL2 | 1 | 2 | 3 | 16 | 4 | 5 | 6 | 25 |
| 3C2-VH4VL3 | 1 | 2 | 3 | 16 | 4 | 5 | 6 | 26 |
| 3C2-VH4VL4 | 1 | 2 | 3 | 16 | 4 | 5 | 6 | 27 |
| 3C2-VH5VL2 | 1 | 2 | 3 | 17 | 4 | 5 | 6 | 25 |
| 3C2-VH5VL3 | 1 | 2 | 3 | 17 | 4 | 5 | 6 | 26 |
| 3C2-VH5VL4 | 1 | 2 | 3 | 17 | 4 | 5 | 6 | 27 |
| 3C2-VH6VL5 | 1 | 2 | 3 | 18 | 4 | 5 | 6 | 28 |
| Mouse and chimeric 56E5 | 7 | 8 | 9 | 19 | 10 | 11 | 12 | 29 |
| 56E5-VH2VL2 | 7 | 8 | 9 | 20 | 10 | 11 | 12 | 30 |
| 56E5-VH2VL3 | 7 | 8 | 9 | 20 | 10 | 11 | 12 | 31 |
| 56E5-VH2VL4 | 7 | 8 | 9 | 20 | 10 | 11 | 12 | 32 |
| 56E5-VH3VL2 | 7 | 8 | 9 | 21 | 10 | 11 | 12 | 30 |
| 56E5-VH3VL3 | 7 | 8 | 9 | 21 | 10 | 11 | 12 | 31 |
| 56E5-VH3VL4 | 7 | 8 | 9 | 21 | 10 | 11 | 12 | 32 |
| 56E5-VH4VL2 | 7 | 8 | 9 | 22 | 10 | 11 | 12 | 30 |
| 56E5-VH4VL3 | 7 | 8 | 9 | 22 | 10 | 11 | 12 | 31 |
| 56E5-VH4VL4 | 7 | 8 | 9 | 22 | 10 | 11 | 12 | 32 |
| 56E5-VH5VL2 | 7 | 8 | 9 | 23 | 10 | 11 | 12 | 30 |
| 56E5-VH5VL3 | 7 | 8 | 9 | 23 | 10 | 11 | 12 | 31 |
| 56E5-VH5VL4 | 7 | 8 | 9 | 23 | 10 | 11 | 12 | 32 |

The heavy chain variable region CDRs and the light chain variable region CDRs in Table 1 have been defined by the Kabat numbering system. However, as is well known in the art, CDR regions can also be determined by other systems such as Chothia, IMGT, AbM, or Contact numbering system/method, based on heavy chain/light chain variable region sequences.

The antibodies of the disclosure may each comprise a heavy chain constant region, such as IgG1 constant region, e.g., human IgG1 constant region having the amino acid sequence of SEQ ID NO: 33, or a functional fragment thereof. The antibodies of the disclosure may each comprise a light chain constant region, such as kappa light chain constant region, e.g., human kappa constant region having the amino acid sequence of SEQ ID NO: 34, or a functional fragment thereof.

The $V_H$ and $V_L$ sequences (or CDR sequences) of other anti-PD-L1 antibodies which bind to human PD-L1 can be "mixed and matched" with the $V_H$ and $V_L$ sequences (or CDR sequences) of the anti-PD-L1 antibody of the present disclosure. Preferably, when $V_H$ and $V_L$ chains (or the CDRs within such chains) are mixed and matched, a VET sequence from a particular $V_H/V_L$ pairing is replaced with a structurally similar VET sequence. Likewise, preferably a $V_L$ sequence from a particular $V_H/V_L$ pairing is replaced with a structurally similar $V_L$ sequence.

In another embodiment, an antibody of the disclosure, or an antigen binding portion thereof, comprises:
(a) the CDR1, CDR2, and CDR3 regions of the heavy chain variable region listed above in Table 1; and
(b) the CDR1, CDR2, and CDR3 regions of the light chain variable region listed above in Table 1 or the CDRs of another anti-PD-L1 antibody, wherein the antibody specifically binds human PD-L1.

In yet another embodiment, the antibody, or antigen binding portion thereof, includes the heavy chain variable CDR2 region of anti-PD-L1 antibody combined with CDRs of other antibodies which bind human PD-L1, e.g., CDR1 and/or CDR3 from the heavy chain variable region, and/or CDR1, CDR2, and/or CDR3 from the light chain variable region of a different anti-PD-L1 antibody.

In addition, it is well known in the art that the CDR3 domain, independently from the CDR1 and/or CDR2 domain(s), alone can determine the binding specificity of an antibody for a cognate antigen and that multiple antibodies can predictably be generated having the same binding specificity based on a common CDR3 sequence. See, e.g., Klimka et al. *British J. of Cancer* 83(2):252-260 (2000); Beiboer et al. *J. Mol. Biol.* 296:833-849 (2000); Rader et al. *Proc. Natl. Acad. Sci. U.S.A.* 95:8910-8915 (1998); Barbas et al. *J. Am. Chem. Soc.* 116:2161-2162 (1994); Barbas et al. *Proc. Natl. Acad. Sci. U.S.A.* 92:2529-2533 (1995); Ditzel et al., *J. Immunol.* 157:739-749 (1996); Berezov et al., *BIAjournal* 8:

Scientific Review 8 (2001); Igarashi et al., J. Biochem (Tokyo) 117:452-7 (1995); Bourgeois et al., J. Virol 72:807-10 (1998); Levi et al., Proc. Natl. Acad. Sci. U.S.A. 90:4374-8 (1993); Polymenis and Stoller, J. Immunol. 152: 5218-5329 (1994) and Xu and Davis, Immunity 13:37-45 (2000). See also, U.S. Pat. Nos. 6,951,646; 6,914,128; 6,090,382; 6,818,216; 6,156,313; 6,827,925; 5,833,943; 5,762,905 and 5,760,185. Each of these references is hereby incorporated by reference in its entirety.

Accordingly, in another embodiment, the antibody or antigen-binding portion thereof of the disclosure comprise the CDR2 of the heavy chain variable region of the anti-PD-L1 antibody and at least the CDR3 of the heavy and/or light chain variable region of the anti-PD-L1 antibody, or the CDR3 of the heavy and/or light chain variable region of another anti-PD-L1 antibody, wherein the antibody or antigen binding portion thereof is capable of specifically binding to human PD-L1. These antibodies or antigen binding portions thereof preferably (a) compete for binding with PD-L1; (b) retain the functional characteristics; (c) bind to the same epitope; and/or (d) have a similar binding affinity as the anti-PD-L1 antibody of the present disclosure. In yet another embodiment, the antibodies or antigen binding portions thereof further may comprise the CDR2 of the light chain variable region of the anti-PD-L1 antibody, or the CDR2 of the light chain variable region of another anti-PD-L1 antibody, wherein the antibody or antigen binding portion thereof is capable of specifically binding to human PD-L1. In another embodiment, the antibodies or antigen binding portions thereof of the disclosure may include the CDR1 of the heavy and/or light chain variable region of the anti-PD-L1 antibody, or the CDR1 of the heavy and/or light chain variable region of another anti-PD-L1 antibody, wherein the antibody or antigen binding portion thereof is capable of specifically binding to human PD-L1.

In another embodiment, an antibody or antigen binding portion thereof of the disclosure comprises a heavy and/or light chain variable region sequences of CDR1, CDR2 and CDR3 sequences which differ from those of the anti-PD-L1 antibodies or antigen binding portions thereof of the present disclosure by one or more conservative modifications. It is understood in the art that certain conservative sequence modification can be made which do not remove antigen binding. See, e.g., Brummell et al., (1993) Biochem 32:1180-8; de Wildt et al., (1997) Prot. Eng. 10:835-41; Komissarov et al., (1997) J. Biol. Chem. 272:26864-26870; Hall et al., (1992) J. Immunol. 149:1605-12; Kelley and O'Connell (1993) Biochem. 32:6862-35; Adib-Conquy et al., (1998) Int. Immunol. 10:341-6 and Beers et al., (2000) Clin. Can. Res. 6:2835-43.

Accordingly, in one embodiment, the antibody or antigen binding portion thereof comprises a heavy chain variable region comprising CDR1, CDR2, and CDR3 sequences and/or a light chain variable region comprising CDR1, CDR2, and CDR3 sequences, wherein:
(a) the heavy chain variable region CDR1 sequence comprises a sequence listed in Table 1 above, and/or conservative modifications thereof; and/or
(b) the heavy chain variable region CDR2 sequence comprises a sequence listed in Table 1 above, and/or conservative modifications thereof; and/or
(c) the heavy chain variable region CDR3 sequence comprises a sequence listed in Table 1 above, and conservative modifications thereof; and/or
(d) the light chain variable region CDR1, and/or CDR2, and/or CDR3 sequences comprise the sequence(s) listed in Table 1 above; and/or conservative modifications thereof; and
(e) the antibody specifically binds human PD-L1.

The antibody or antigen binding portion thereof of the present disclosure possesses one or more of the following functional properties described above, such as high affinity binding to human PD-L1, and reduced or eliminated ability to induce antibody dependent cell mediated cytotoxicity (ADCC) against PD-L1 positive cells.

In various embodiments, the antibody or antigen binding portion thereof, of the disclosure can be, for example, mouse, chimeric, human, or humanized.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the disclosure by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within the CDR regions of an antibody of the disclosure can be replaced with other amino acid residues from the same side chain family and the altered antibody can be tested for retained function (i.e., the functions set forth above) using the functional assays described herein.

The antibody of the disclosure can be prepared using an antibody having one or more of the $V_H/V_L$ sequences of the anti-PD-L1 antibody of the present disclosure as starting material to engineer a modified antibody. An antibody can be engineered by modifying one or more residues within one or both variable regions (i.e., $V_H$ and/or $V_L$), for example within one or more CDR regions and/or within one or more framework regions. Additionally or alternatively, an antibody can be engineered by modifying residues within the constant region(s), for example to alter the effector function (s) of the antibody.

In certain embodiments, CDR grafting can be used to engineer variable regions of antibodies. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, e.g., Riechmann et al., (1998) Nature 332:323-327; Jones et al., (1986) *Nature* 321:522-525; Queen et al., (1989) *Proc. Natl. Acad.* See also U.S.A. 86:10029-10033; U.S. Pat. Nos. 5,225,539; 5,530,101; 5,585,089; 5,693,762 and 6,180,370).

Accordingly, another embodiment of the disclosure pertains to an isolated monoclonal antibody, or antigen binding portion thereof, comprising a heavy chain variable region comprising CDR1, CDR2, and CDR3 sequences comprising the sequences of the present disclosure, as described above, and/or a light chain variable region comprising CDR1, CDR2, and CDR3 sequences comprising the sequences of the present disclosure, as described above. While these antibodies contain the $V_H$ and $V_L$ CDR sequences of the monoclonal antibody of the present disclosure, they can contain different framework sequences.

Such framework sequences can be obtained from public DNA databases or published references that include germline antibody gene sequences. For example, germline DNA sequences for human heavy and light chain variable region genes can be found in the "VBase" human germline sequence database (available on the Internet at mrc-cpe.cam.ac.uk/vbase), as well as in Kabat et al., (1991), cited supra; Tomlinson et al., (1992) *J. Mol. Biol.* 227:776-798; and Cox et al., (1994) *Eur. J. Immunol.* 24:827-836; the contents of each of which are expressly incorporated herein by reference. As another example, the germline DNA sequences for human heavy and light chain variable region genes can be found in the Genbank database. For example, the following heavy chain germline sequences found in the HCo7 HuMAb mouse are available in the accompanying Genbank Accession Nos.: 1-69 (NG-0010109, NT-024637 & BC070333), 3-33 (NG-0010109 & NT-024637) and 3-7 (NG-0010109 & NT-024637). As another example, the following heavy chain germline sequences found in the HCo12 HuMAb mouse are available in the accompanying Genbank Accession Nos.: 1-69 (NG-0010109, NT-024637 & BC070333), 5-51 (NG-0010109 & NT-024637), 4-34 (NG-0010109 & NT-024637), 3-30.3 (CAJ556644) & 3-23 (AJ406678).

Antibody protein sequences are compared against a compiled protein sequence database using one of the sequence similarity searching methods called the Gapped BLAST (Altschul et al., (1997), supra), which is well known to those skilled in the art.

Preferred framework sequences for use in the antibodies of the disclosure are those that are structurally similar to the framework sequences used by antibodies of the disclosure. The $V_H$ CDR1, CDR2, and CDR3 sequences can be grafted onto framework regions that have the identical sequence as that found in the germline immunoglobulin gene from which the framework sequence derives, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370).

Another type of variable region modification is to mutate amino acid residues within the $V_H$ and/or $V_L$ CDR1, CDR2 and/or CDR3 regions to thereby improve one or more binding properties (e.g., affinity) of the antibody of interest. Site-directed mutagenesis or PCR-mediated mutagenesis can be performed to introduce the mutation(s) and the effect on antibody binding, or other functional property of interest, can be evaluated in in vitro or in vivo assays as known in the art. Preferably conservative modifications (as known in the art) are introduced. The mutations can be amino acid substitutions, additions or deletions, but are preferably substitutions. Moreover, typically no more than one, two, three, four or five residues within a CDR region are altered.

Accordingly, in another embodiment, the disclosure provides isolated anti-PD-L1 monoclonal antibodies, or antigen binding portions thereof, comprising a heavy chain variable region comprising: (a) a $V_H$ CDR1 region comprising the sequence of the present disclosure, or an amino acid sequence having one, two, three, four or five amino acid substitutions, deletions or additions; (b) a $V_H$ CDR2 region comprising the sequence of the present disclosure, or an amino acid sequence having one, two, three, four or five amino acid substitutions, deletions or additions; (c) a $V_H$ CDR3 region comprising the sequence of the present disclosure, or an amino acid sequence having one, two, three, four or five amino acid substitutions, deletions or additions; (d) a $V_L$ CDR1 region comprising the sequence of the present disclosure, or an amino acid sequence having one, two, three, four or five amino acid substitutions, deletions or additions; (e) a $V_L$ CDR2 region comprising the sequence of the present disclosure, or an amino acid sequence having one, two, three, four or five amino acid substitutions, deletions or additions; and (f) a $V_L$ CDR3 region comprising the sequence of the present disclosure, or an amino acid sequence having one, two, three, four or five amino acid substitutions, deletions or additions.

Engineered antibodies of the disclosure include those in which modifications have been made to framework residues within $V_H$ and/or $V_L$, e.g. to improve the properties of the antibody. Typically, such framework modifications are made to decrease the immunogenicity of the antibody. For example, one approach is to "backmutate" one or more framework residues to the corresponding germline sequence. More specifically, an antibody that has undergone somatic mutation can contain framework residues that differ from the germline sequence from which the antibody is derived. Such residues can be identified by comparing the antibody framework sequences to the germline sequences from which the antibody is derived.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Patent Publication No. 20030153043.

In addition, or as an alternative to modifications made within the framework or CDR regions, antibodies of the disclosure can be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the disclosure can be chemically modified (e.g., one or more chemical moieties can be attached to the antibody) or be modified to alter its glycosylation, again to alter one or more functional properties of the antibody.

In one embodiment, the hinge region of $C_{H1}$ is modified in such that the number of cysteine residues in the hinge region is altered, e.g., increased or decreased. This approach is described further in U.S. Pat. No. 5,677,425. The number of cysteine residues in the hinge region of $C_{H1}$ is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the $C_{H2}$-$C_{H3}$ domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745.

In still another embodiment, the glycosylation of an antibody is modified. For example, a glycosylated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. See, e.g., U.S. Pat. Nos. 5,714,350 and 6,350,861.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the disclosure to thereby produce an antibody with altered glycosylation. For example, the cell lines Ms704, Ms705, and Ms709 lack the fucosyltransferase gene, FUT8 ($\alpha$(1,6)-fucosyltransferase), such that antibodies expressed in the Ms704, Ms705, and Ms709 cell lines lack fucose on their carbohydrates. The Ms704, Ms705, and Ms709 FUT8−/− cell lines were created by the targeted disruption of the FUT8 gene in CHO/DG44 cells using two replacement vectors (see U.S. Patent Publication No. 20040110704 and Yamane-Ohnuki et al., (2004) Biotechnol Bioeng 87:614-22). As another example, EP 1,176,195 describes a cell line with a functionally disrupted FUT8 gene, which encodes a fucosyl transferase, such that antibodies expressed in such a cell line exhibit hypofucosylation by reducing or eliminating the $\alpha$-1,6 bond-related enzyme. EP 1,176,195 also describes cell lines which have a low enzyme activity for adding fucose to the N-acetylglucosamine that binds to the Fc region of the antibody or does not have the enzyme activity, for example the rat myeloma cell line YB2/0 (ATCC CRL 1662). PCT Publication WO 03/035835 describes a variant CHO cell line, Lec13 cells, with reduced ability to attach fucose to Asn(297)-linked carbohydrates, also resulting in hypofucosylation of antibodies expressed in that host cell (see also Shields et al., (2002) J. Biol. Chem. 277: 26733-26740). Antibodies with a modified glycosylation profile can also be produced in chicken eggs, as described in PCT Publication WO 06/089231. Alternatively, antibodies with a modified glycosylation profile can be produced in plant cells, such as Lemna. PCT Publication WO 99/54342 describes cell lines engineered to express glycoprotein-modifying glycosyl transferases (e.g., $\beta$(1,4)-N-acetylglucosaminyltransferase III (GnTIII)) such that antibodies expressed in the engineered cell lines exhibit increased bisecting GlcNac structures which results in increased ADCC activity of the antibodies (see also Umana et al., (1999) Nat. Biotech. 17:176-180). Alternatively, the fucose residues of the antibody can be cleaved off using a fucosidase enzyme; e.g., the fucosidase $\alpha$-L-fucosidase removes fucosyl residues from antibodies (Tarentino et al., (1975) Biochem. 14:5516-23).

Another modification of the antibodies herein that is contemplated by this disclosure is pegylation. An antibody can be pegylated to, for example, increase the biological (e.g., serum) half-life of the antibody. To pegylate an antibody, the antibody, or fragment thereof, typically is reacted with polyethylene glycol (PEG), such as a reactive ester or aldehyde derivative of PEG, under conditions in which one or more PEG groups become attached to the antibody or antibody fragment. Preferably, the pegylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono ($C_1$-$C_{10}$) alkoxy- or aryloxy-polyethylene glycol or polyethylene glycol-maleimide. In certain embodiments, the antibody to be pegylated is an aglycosylated antibody. Methods for pegylating proteins are known in the art and can be applied to the antibodies of the disclosure. See, e.g., EPO 154 316 and EP 0 401 384.

Antibodies of the disclosure can be characterized by their various physical properties, to detect and/or differentiate different classes thereof.

For example, antibodies can contain one or more glycosylation sites in either the light or heavy chain variable region. Such glycosylation sites may result in increased immunogenicity of the antibody or an alteration of the pK of the antibody due to altered antigen binding (Marshall et al (1972) Annu Rev Biochem 41:673-702; Gala and Morrison (2004) J Immunol 172:5489-94; Wallick et al (1988) J Exp Med 168:1099-109; Spiro (2002) Glycobiology 12:43R-56R; Parekh et al (1985) Nature 316:452-7; Mimura et al., (2000) Mol Immunol 37:697-706). Glycosylation has been known to occur at motifs containing an N-X-S/T sequence. In some instances, it is preferred to have an anti-PD-L1 antibody that does not contain variable region glycosylation. This can be achieved either by selecting antibodies that do not contain the glycosylation motif in the variable region or by mutating residues within the glycosylation region.

In a preferred embodiment, the antibodies do not contain asparagine isomerism sites. The deamidation of asparagine may occur on N-G or D-G sequences and result in the creation of an isoaspartic acid residue that introduces a kink into the polypeptide chain and decreases its stability (isoaspartic acid effect).

Each antibody will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8. There is speculation that antibodies with a pI outside the normal range may have some unfolding and instability under in vivo conditions. Thus, it is preferred to have an anti-PD-L1 antibody that contains a pI value that falls in the normal range. This can be achieved either by selecting antibodies with a pI in the normal range or by mutating charged surface residues.

In another aspect, the disclosure provides nucleic acid molecules that encode heavy and/or light chain variable regions, or CDRs, of the antibodies of the disclosure. The nucleic acids can be present in whole cells, in a cell lysate, or in a partially purified or substantially pure form. A nucleic acid is "isolated" or "rendered substantially pure" when purified away from other cellular components or other contaminants, e.g., other cellular nucleic acids or proteins, by standard techniques. A nucleic acid of the disclosure can be, e.g., DNA or RNA and may or may not contain intronic sequences. In a preferred embodiment, the nucleic acid is a cDNA molecule.

Nucleic acids of the disclosure can be obtained using standard molecular biology techniques. For antibodies expressed by hybridomas (e.g., hybridomas prepared from transgenic mice carrying human immunoglobulin genes as described further below), cDNAs encoding the light and heavy chains of the antibody made by the hybridoma can be obtained by standard PCR amplification or cDNA cloning techniques. For antibodies obtained from an immunoglobulin gene library (e.g., using phage display techniques), a nucleic acid encoding such antibodies can be recovered from the gene library.

Preferred nucleic acids molecules of the disclosure include those encoding the $V_H$ and $V_L$ sequences of the PD-L1 monoclonal antibody or the CDRs. Once DNA fragments encoding $V_H$ and $V_L$ segments are obtained, these DNA fragments can be further manipulated by standard recombinant DNA techniques, for example to convert the variable region genes to full-length antibody chain genes, to Fab fragment genes or to a scFv gene. In these manipulations, a $V_L$- or $V_H$-encoding DNA fragment is operatively linked to another DNA fragment encoding another protein, such as an antibody constant region or a flexible linker. The term "operatively linked", as used in this context, is intended to mean that the two DNA fragments are joined such that the amino acid sequences encoded by the two DNA fragments remain in-frame.

The isolated DNA encoding the $V_H$ region can be converted to a full-length heavy chain gene by operatively linking the $V_H$-encoding DNA to another DNA molecule encoding heavy chain constant regions ($C_{H1}$, $C_{H2}$ and $C_{H3}$). The sequences of human heavy chain constant region genes are known in the art and DNA fragments encompassing these regions can be obtained by standard PCR amplification. The heavy chain constant region can be an IgG1, IgG2, IgG3, IgG4, IgA, IgE, IgM or IgD constant region, but most preferably is an IgG1 or IgG4 constant region. For a Fab fragment heavy chain gene, the $V_H$-encoding DNA can be operatively linked to another DNA molecule encoding only the heavy chain $C_{H1}$ constant region.

The isolated DNA encoding the $V_L$ region can be converted to a full-length light chain gene (as well as a Fab light chain gene) by operatively linking the $V_L$-encoding DNA to another DNA molecule encoding the light chain constant region, $C_L$. The sequences of human light chain constant region genes are known in the art and DNA fragments encompassing these regions can be obtained by standard PCR amplification. In preferred embodiments, the light chain constant region can be a kappa or lambda constant region.

To create a scFv gene, the $V_H$- and $V_L$-encoding DNA fragments are operatively linked to another fragment encoding a flexible linker, e.g., encoding the amino acid sequence (Gly4-Ser)3, such that the $V_H$ and $V_L$ sequences can be expressed as a contiguous single-chain protein, with the $V_L$ and $V_H$ regions joined by the flexible linker (see e.g., Bird et al., (1988) *Science* 242:423-426; Huston et al., (1988) *Proc. Natl. Acad. Sci. USA* 85:5879-5883; McCafferty et al., (1990) *Nature* 348:552-554).

Monoclonal antibodies (mAbs) of the present disclosure can be produced using the well-known somatic cell hybridization (hybridoma) technique of Kohler and Milstein (1975) *Nature* 256: 495. Other embodiments for producing monoclonal antibodies include viral or oncogenic transformation of B lymphocytes and phage display techniques. Chimeric or humanized antibodies are also well known in the art. See e.g., U.S. Pat. Nos. 4,816,567; 5,225,539; 5,530,101; 5,585,089; 5,693,762 and 6,180,370, the contents of which are specifically incorporated herein by reference in their entirety.

Antibodies of the disclosure also can be produced in a host cell transfectoma using, for example, a combination of recombinant DNA techniques and gene transfection methods as is well known in the art (e.g., Morrison, S. (1985) *Science* 229:1202). In one embodiment, DNA encoding partial or full-length light and heavy chains obtained by standard molecular biology techniques is inserted into one or more expression vectors such that the genes are operatively linked to transcriptional and translational regulatory sequences. In this context, the term "operatively linked" is intended to mean that an antibody gene is ligated into a vector such that transcriptional and translational control sequences within the vector serve their intended function of regulating the transcription and translation of the antibody gene.

The term "regulatory sequence" is intended to include promoters, enhancers and other expression control elements (e.g., polyadenylation signals) that control the transcription or translation of the antibody genes. Such regulatory sequences are described, e.g., in Goeddel (Gene Expression Technology. Methods in Enzymology 185, Academic Press, San Diego, Calif. (1990)). Preferred regulatory sequences for mammalian host cell expression include viral elements that direct high levels of protein expression in mammalian cells, such as promoters and/or enhancers derived from cytomegalovirus (CMV), Simian Virus 40 (SV40), adenovirus, e.g., the adenovirus major late promoter (AdMLP) and polyoma. Alternatively, nonviral regulatory sequences can be used, such as the ubiquitin promoter or β-globin promoter. Still further, regulatory elements composed of sequences from different sources, such as the SRα promoter system, which contains sequences from the SV40 early promoter and the long terminal repeat of human T cell leukemia virus type 1 (Takebe et al., (1988) Mol. Cell. Biol. 8:466-472). The expression vector and expression control sequences are chosen to be compatible with the expression host cell used.

The antibody light chain gene and the antibody heavy chain gene can be inserted into the same or separate expression vectors. In preferred embodiments, the variable regions are used to create full-length antibody genes of any antibody isotype by inserting them into expression vectors already encoding heavy chain constant and light chain constant regions of the desired isotype such that the $V_H$ segment is operatively linked to the $C_H$ segment(s) within the vector and the $V_L$ segment is operatively linked to the $C_L$ segment within the vector. Additionally or alternatively, the recombinant expression vector can encode a signal peptide that facilitates secretion of the antibody chain from a host cell. The antibody chain gene can be cloned into the vector such that the signal peptide is linked in-frame to the amino terminus of the antibody chain gene. The signal peptide can be an immunoglobulin signal peptide or a heterologous signal peptide (i.e., a signal peptide from a non-immunoglobulin protein).

In addition to the antibody chain genes and regulatory sequences, the recombinant expression vectors of the disclosure can carry additional sequences, such as sequences that regulate replication of the vector in host cells (e.g., origins of replication) and selectable marker genes. The selectable marker gene facilitates selection of host cells into which the vector has been introduced (see, e.g., U.S. Pat. Nos. 4,399,216; 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr-host cells with methotrexate selection/amplification) and the neo gene (for G418 selection).

For expression of the light and heavy chains, the expression vector(s) encoding the heavy and light chains is transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is theoretically possible to express the antibodies of the disclosure in either prokaryotic or eukaryotic host cells, expression of antibodies in eukaryotic cells, and most preferably mammalian host cells, is the most preferred because such eukaryotic cells, and in particular mammalian cells, are more likely than prokaryotic cells to assemble and secrete a properly folded and immunologically active antibody.

Preferred mammalian host cells for expressing the recombinant antibodies of the disclosure include Chinese Hamster Ovary (CHO cells) (including dhfr-CHO cells, described in Urlaub and Chasin, (1980) *Proc. Natl. Acad. Sci. USA* 77:4216-4220, used with a DHFR selectable marker, e.g., as described in R. J. Kaufman and P. A. Sharp (1982) *J. Mol. Biol.* 159:601-621), NSO myeloma cells, COS cells and SP2 cells. In particular for use with NSO myeloma cells, another preferred expression system is the GS gene expression system disclosed in WO 87/04462, WO 89/01036 and EP 338,841. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

The antibody or antigen binding portion thereof of the disclosure may be conjugated to a therapeutic agent to form an immunoconjugate such as an antibody-drug conjugate (ADC). Suitable therapeutic agents include cytotoxins, alkylating agents, DNA minor groove binders, DNA intercalators, DNA crosslinkers, histone deacetylase inhibitors, nuclear export inhibitors, proteasome inhibitors, topoisomerase I or II inhibitors, heat shock protein inhibitors, tyrosine kinase inhibitors, antibiotics, and anti-mitotic agents. In the ADC, the antibody and therapeutic agent preferably are conjugated via a linker cleavable such as a peptidyl, disulfide, or hydrazone linker. More preferably, the linker is a peptidyl linker such as Val-Cit, Ala-Val, Val-Ala-Val, Lys-Lys, Ala-Asn-Val, Val-Leu-Lys, Ala-Ala-Asn, Cit-Cit, Val-Lys, Lys, Cit, Ser, or Glu. The ADCs can be prepared as described in U.S. Pat. Nos. 7,087,600; 6,989,452; and 7,129,261; PCT Publications WO 02/096910; WO 07/038,658; WO 07/051,081; WO 07/059,404; WO 08/083, 312; and WO 08/103,693; U.S. Patent Publications 20060024317; 20060004081; and 20060247295; the disclosures of which are incorporated herein by reference.

In another aspect, the present disclosure features a bispecific molecule comprising the antibody or antigen binding portion thereof of the disclosure linked to at least one other functional molecule, e.g., another peptide or protein (e.g., another antibody or ligand for a receptor) to generate a bispecific molecule that binds to at least two different binding sites or target molecules. Thus, as used herein, the "bispecific molecule" includes molecules that have three or more specificities.

The bispecific molecules may be in many different formats and sizes. At one end of the size spectrum, a bispecific molecule retains the traditional antibody format, except that, instead of having two binding arms of identical specificity, it has two binding arms each having a different specificity. At the other extreme are bispecific molecules consisting of two single-chain antibody fragments (scFv's) linked by a peptide chain, a so-called Bs(scFv) 2 construct. Intermediate-sized bispecific molecules include two different F(ab) fragments linked by a peptidyl linker. Bispecific molecules of these and other formats can be prepared by genetic engineering, somatic hybridization, or chemical methods. See, e.g., Kufer et al, cited supra; Cao and Suresh, *Bioconjugate Chemistry,* 9 (6), 635-644 (1998); and van Spriel et al., *Immunology Today,* 21 (8), 391-397 (2000), and the references cited therein.

The disclosure provides a chimeric antigen receptor comprising an anti-PD-L1 single chain variable fragment (scFv) comprising the heavy and light chain variable regions and/or CDRs of the disclosure.

The chimeric antigen receptor may comprise (a) an extracellular antigen recognition domain containing the anti-PD-L1 scFv, (b) a transmembrane domain, and (c) an intracellular signaling domain.

An oncolytic virus preferentially infects and kills cancer cells. The antibody or antigen binding portion thereof of the disclosure may be used in conjunction with the oncolytic virus. Alternatively, an oncolytic virus encoding the antibody or antigen binding portion thereof of the disclosure can be introduced into human body.

In another aspect, the present disclosure provides a pharmaceutical composition comprising the antibody or antigen binding portion thereof, the immunoconjugate, the bispecific molecule, the immune cell carrying the chimeric antigen receptor, the oncolytic virus, the nucleic acid molecule, the expression vector, and/or the host cell of the present disclosure formulated together with a pharmaceutically acceptable carrier. The composition may optionally contain one or more additional pharmaceutically active ingredients, such as an anti-tumor agent, an anti-infective agent, or an agent for immunity enhancement. The pharmaceutical composition of the disclosure may be administered in a combination therapy with, for example, an anti-tumor agent, an anti-infective agent, or an agent for immunity enhancement.

The pharmaceutical composition may comprise any number of excipients. Excipients that can be used include carriers, surface active agents, thickening or emulsifying agents, solid binders, dispersion or suspension aids, solubilizers, colorants, flavoring agents, coatings, disintegrating agents, lubricants, sweeteners, preservatives, isotonic agents, and combinations thereof. The selection and use of suitable excipients is taught in Gennaro, ed., Remington: *The Science and Practice of Pharmacy,* 20th Ed. (Lippincott Williams & Wilkins 2003), the disclosure of which is incorporated herein by reference.

Preferably, the pharmaceutical composition is suitable for intravenous, intramuscular, subcutaneous, parenteral, spinal or epidermal administration (e.g., by injection or infusion). Depending on the route of administration, the active ingredient can be coated in a material to protect it from the action of acids and other natural conditions that may inactivate it. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion. Alternatively, an antibody of the disclosure can be administered via a non-parenteral route, such as a topical, epidermal or mucosal route of administration, e.g., intranasally, orally, vaginally, rectally, sublingually or topically.

The pharmaceutical composition may be in the form of a sterile aqueous solution or dispersion. The pharmaceutical composition may also be formulated in a microemulsion, liposome, or other ordered structure suitable for high drug concentration.

The amount of the active ingredient which can be combined with a carrier material to produce a single dosage form will vary depending upon the subject being treated and the particular mode of administration and will generally be that amount of the composition which produces a therapeutic effect. Generally, out of one hundred percent, this amount will range from about 0.01% to about 99% of active ingredient in combination with a pharmaceutically acceptable carrier.

Dosage regimens are adjusted to provide the optimum desired response (e.g., a therapeutic response). For example, a single bolus can be administered, several divided doses can be administered over time or the dose can be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active ingredient calculated to produce the desired therapeutic effect in association with the required pharmaceutical carrier. Alternatively, antibody can be administered as a sustained release formulation, in which case less frequent administration is required.

For administration of the antibody or antigen binding portion thereof, the dosage may range from about 0.0001 to 100 mg/kg body weight. An exemplary treatment regime entails administration once per week. Preferred dosage regimens for an anti-PD-L1 antibody of the disclosure include intravenous administration.

A "therapeutically effective dosage" of an anti-PD-L1 antibody of the disclosure preferably results in a decrease in severity of disease symptoms, an increase in frequency and duration of disease symptom-free periods, or a prevention of impairment or disability due to the disease affliction. For example, for the treatment of tumor-bearing subjects, a "therapeutically effective dosage" preferably inhibits tumor growth by at least about 20%, more preferably by at least about 40%, even more preferably by at least about 60%, and still more preferably by at least about 80% relative to untreated subjects. A therapeutically effective amount of a therapeutic antibody can decrease tumor size, or otherwise ameliorate symptoms in a subject, which is typically a human or can be another mammal.

The pharmaceutical composition can be a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. See, e.g., Sustained and Controlled Release Drug Delivery Systems, J. R. Robinson, ed., Marcel Dekker, Inc., New York, 1978.

Therapeutic compositions can be administered via medical devices such as (1) needleless hypodermic injection devices (e.g., U.S. Pat. Nos. 5,399,163; 5,383,851; 5,312,335; 5,064,413; 4,941,880; 4,790,824; and 4,596,556); (2) micro-infusion pumps (U.S. Pat. No. 4,487,603); (3) transdermal devices (U.S. Pat. No. 4,486,194); (4) infusion apparatuses (U.S. Pat. Nos. 4,447,233 and 4,447,224); and (5) osmotic devices (U.S. Pat. Nos. 4,439,196 and 4,475,196); the disclosures of which are incorporated herein by reference.

In certain embodiments, the monoclonal antibodies of the disclosure can be formulated to ensure proper distribution in vivo. For example, to ensure that the therapeutic antibody of the disclosure cross the blood-brain barrier, they can be formulated in liposomes, which may additionally comprise targeting moieties to enhance selective transport to specific cells or organs. See, e.g. U.S. Pat. Nos. 4,522,811; 5,374,548; 5,416,016; and 5,399,331; V. V. Ranade (1989) *J. Clin. Pharmacol.* 29:685; Umezawa et al., (1988) *Biochem. Biophys. Res. Commun.* 153:1038; Bloeman et al., (1995) *FEBS Lett.* 357:140; M. Owais et al., (1995) *Antimicrob. Agents Chemother.* 39:180; Briscoe et al., (1995) *Am. J. Physiol.* 1233:134; Schreier et al., (1994) *J. Biol. Chem.* 269:9090; Keinanen and Laukkanen (1994) *FEBS Lett.* 346:123; and Killion and Fidler (1994) *Immunomethods* 4:273.

The pharmaceutical composition of the disclosure may have numerous in vitro and in vivo utilities involving, for example, treatment and/or prevention of cancers and infectious diseases. The pharmaceutical composition of the disclosure may be administered to human subjects, to inhibit tumor growth, or reduce or eliminate pathogens.

Given the ability of anti-PD-L1 antibodies of the disclosure to inhibit proliferation and survival of cancer cells, the disclosure provides methods for inhibiting growth of tumor cells in a subject comprising administering to the subject the pharmaceutical composition of the disclosure such that growth of the tumor is inhibited in the subject. Non-limiting examples of tumors that can be treated by antibodies of the disclosure include, but not limited to, melanoma, non-small cell lung cancer, renal cell carcinoma, Hodgkin lymphoma, bladder cancer, head and neck cancer, neuroendocrine tumor, mantle cell lymphoma, diffuse large B-cell lymphoma, and follicular lymphoma, original and/or metastatic. Additionally, refractory or recurrent malignancies may be inhibited using the pharmaceutical composition of the disclosure.

In another aspect, as the pharmaceutical composition of the disclosure may reduce or eliminate the pathogens, the disclosure provides a method for treating an infectious disease in a subject in need thereof, comprising administering to the subject the pharmaceutical composition of the disclosure. The infectious disease may be caused by viral, bacterial, fungal, or mycoplasma infection. The infectious disease may be a chronic hepatitis B virus (HBV), hepatitis C virus (HCV), human immunodeficiency virus (HIV), or simian immunodeficiency virus (SIV) infection.

In another aspect, the disclosure provides methods of combination therapy in which the pharmaceutical composition of the disclosure is co-administered with one or more additional antibodies or non-antibody agents that are effective in inhibiting tumor growth in a subject. In one embodiment, the disclosure provides a method for inhibiting tumor growth in a subject comprising administering to the subject the pharmaceutical composition of the disclosure with one or more additional antibodies, such as an anti-VISTA antibody, an anti-LAG-3 antibody, an anti-PD-1 antibody and/or an anti-CTLA-4 antibody. The pharmaceutical composition of the disclosure may be used in combination with a chemotherapeutic agent, which is toxic to cells. Other therapies that may be combined with anti-PD-L1 antibody includes, but not limited to, interleukin-2 (IL-2) administration, radiation, surgery, or hormone deprivation. In certain embodiments, the subject is human.

The pharmaceutical composition of the disclosure may be used in combination with one or more other antibodies or non-antibody agents, to effectively reduce or eliminate pathogens in a subject, such as viruses, bacteria, fungi, or mycoplasmas. For example, the pharmaceutical composition of the disclosure may be used with an anti-infectious agent, including, but not limited to, an anti-virus agent, an anti-bacterial agent, an anti-fungal agent, and an anti-mycoplasma agent.

The combination of therapeutic agents discussed herein can be administered concurrently as a single composition in a pharmaceutically acceptable carrier, or concurrently as separate compositions with each agent in a pharmaceutically acceptable carrier. In another embodiment, the combination of therapeutic agents can be administered sequentially.

Furthermore, if more than one dose of the combination therapy is administered sequentially, the order of the sequential administration can be reversed or kept in the same order at each time point of administration, sequential administrations can be combined with concurrent administrations, or any combination thereof.

The present disclosure is further illustrated by the following examples, which should not be construed as further limiting. The contents of all figures and all references, Genbank sequences, patents and published patent applications cited throughout this application are expressly incorporated herein by reference.

EXAMPLES

Example 1. Construction of HEK293A Cell Lines Stably Expressing Human, Monkey or Mouse PD-L1

Cell lines stably overexpressing human, monkey or mouse PD-L1 were constructed using HEK293A cells (Cobioer, NJ, China). Briefly, cDNA sequences respectively encoding human, monkey and mouse PD-L1 proteins (amino acid sequences set forth in SEQ ID NOs: 35, 36 and 37, respectively) were synthesized, and then subcloned into pLV-EGFP(2A)-Puro vectors. Lentiviruses were generated in HEK-293T cells (Cobioer, NJ, China) by cotransfection of pLV-EGFP(2A)-Puro-PD-L1, psPAX and pMD2.G plasmids, according to the instruction in Lipofectamine 3000 kit (Thermo Fisher Scientific, US). Three days post cotransfection, the lentiviruses were harvested from the cell culture medium (DMEM medium (Cat #:SH30022.01, Gibco) with 10% FBS (Cat #:FND500, Excell)). Finally, HEK293A cells were infected with the lentiviruses to generate HEK293A cell lines stably expressing human, monkey and mouse PD-L1 respectively, namely HEK293A/human PD-L1 cells, HEK293A/monkey PD-L1 cells and HEK293A/mouse PD-L1 cells. Transfected HEK293A cells were then cultured in medium (DMEM+10% FBS) containing 0.2 µg/ml puromycin (Cat #:A11138-03, Gibco) for 7 days. The expressions of human PD-L1 and cynomolgus PD-L1 were confirmed by FACS using a commercially available anti-PD-L1 antibody (PE anti-human PD-L1 Antibody, Cat #:393607, Biolegend, US). Similarly, the expression of mouse PD-L1 was confirmed by FACS using a commercially available anti-mouse PD-L1 antibody (PE anti-mouse PD-L1 Antibody, Cat #:124307, Biolegend, US).

Example 2. Generation of Hybridoma Cell Lines Producing Monoclonal Mouse Antibodies Against Human PD-L1

Murine anti-human PD-L1 monoclonal antibodies (mAbs) were generated using the conventional hybridoma fusion technology with some modifications as follows.

Immunization

Ten BALB/c mice (Beijing Vital River Laboratory Animal Technology Co., Ltd, Beijing, China) were injected with recombinant human PD-L1 (ECD)-hFc (Cat #:10084-H02H, Sino Biological, CN) and recombinant cynomolgus PD-L1 (ECD)-hFc (Cat #:90251-C02H, Sino Biological, CN) following the scheme in Table 2 below. The human PD-L1 (ECD)-hFc and cynomolgus PD-L1 (ECD)-hFc were emulsified by sonication with an equal volume of Complete Freund's Adjuvant (Cat #:F5881-10*10 ML, SIGMA, US), Incomplete Freund's Adjuvant (Cat #:F5506-6*10 ML, SIGMA, US), or PBS.

TABLE 2

| | Immunization scheme | | | | |
|---|---|---|---|---|---|
| | Primary | 1st Boost | 2nd Boost | 3rd Boost | Final Boost |
| | | | Day | | |
| | 0 | 14 | 28 | 42 | 56 |
| Immunogen and dose | Human PD-L1 (ECD)-hFc (50 µg/mouse) | Human PD-L1 (ECD)-hFc (50 µg/mouse) | Cynomolgus PD-L1 (ECD)-hFc (50 µg/mouse) | Human PD-L1 (ECD)-hFc (50 µg/mouse) | Cynomolgus PD-L1 (ECD)-hFc (25 µg/mouse) + Human PD-L1(ECD)-hFc (25 µg/mouse) |
| Adjuvant | Complete Freund's | Incomplete Freund's | Incomplete Freund's | Incomplete Freund's | PBS |
| Immunization | Intraperitoneal injection (i.p.) | i.p. | i.p. | i.p. | Intravenous injection (i.v.) |

One week after each boost, 50 µl murine serum was collected from each mouse for titer determination by ELISA using the recombinant human PD-L1 (ECD)-his (Cat #:10084-H08H, Sino Biological, CN) and cyno PD-L1 (ECD)-hFc (Cat #:90251-C02H, Sino Biological, CN). Titer determination was also done by FACS using HEK293A cells respectively overexpressing human PD-L1, cynomolgus PD-L1 and mouse PD-L1 as prepared in Example 1.

Based on the ELISA and FACS results after the final boost, all the ten mice were used for hybridoma cell line generation.

Generation of Hybridoma Cell Lines

Hybridoma cell lines were generated using the conventional hybridoma fusion technology with minor modifications as follows.

Four days after the final boost, mice were sacrificed, and spleens were collected and prepared as single cell suspensions in PBS. The spleenocytes were washed for three times with DMEM medium (Cat #:SH30243.01B, Hyclone, US). Viable myeloma cells SP2/0 (CRL-1581, ATCC, US) at the log-phase were mixed with the murine spleenocytes at a ratio of 1:4. The cells were then washed twice and then cell fusion was performed with PEG (Cat #:P7181, Sigma, US). The post-fusion cells were washed with DMEM medium for three times and suspended in cell growth medium (RPMI medium 1640 (Cat #:C22400500CP, Gibco)) supplemented with 10% FBS and 1× HAT (Cat #:H0262, Sigma). The cell suspensions were plated onto 96 well cell culture plates, 200 µl per well, containing about $5 \times 10^4$ cells, and incubated in a 37° C. humidified 5% $CO_2$ incubator for 7 days. Then, the growth medium was replaced by fresh one supplemented with 10% FBS and 1× HAT. Two to three days later, cell culture supernatants were collected for hybridoma cell screening by ELISA and FACS.

Screening of Hybridoma Cell Lines by ELISA

High-throughput ELISA binding assay was performed to screen for hybridoma clones producing monoclonal antibodies binding to human PD-L1, using human PD-L1 (ECD)-his (Cat #:10084-H08H, Sino Biological, CN). The hybridoma clones that produced antibodies binding to human PD-L1 were further tested for their abilities to cross-react with cynomolgus PD-L1 using cynomolgus PD-L1 (ECD)-hFc (Cat #:90251-C02H, Sino Biological, CN).

With the ELISA assays, 249 hybridoma clones were identified to have specific binding to both human and monkey PD-L1.

Screening of Hybridoma Cell Lines by FACS

The 249 hybridoma clones were further tested for their binding capabilities to human, cynomolgus and mouse PD-L1s expressed on HEK293A cells, using the HEK293A/human PD-L1 cells, HEK293A/monkey PD-L1 cells and HEK293A/mouse PD-L1 cells as prepared in Example 1.

Based on the FACS screening, 88 positive clones were obtained that displayed high binding capabilities to both HEK293A/human PD-L1 cells and HEK293A/monkey PD-L1 cells.

Subcloning of Hybridoma Clones Producing Anti-PD-L1 Antibodies

The 88 hybridoma clones were subject to 2 rounds of subcloning. During the subcloning, multiple subclones (n>3) from each parent clone were selected and tested by ELISA and FACS assays as described above. The subclones selected through this process were defined as hybridoma cells producing monoclonal antibodies. Finally, 79 subclones (one subclone from each parent clone) having high binding capabilities to both human and monkey PD-L1 were obtained.

Example 3. Purification of Mouse Anti-PD-L1 Monoclonal Antibodies

From 79 clones obtained in Example 2, 10 with relatively high binding capabilities to human and monkey PD-L1s were further characterized. Monoclonal mouse antibodies from the 10 clones were firstly purified. Briefly, hybridoma cells of each subclone were grown in T175 cell culture flasks each having 100 ml fresh serum-free medium (Cat #:12045-076, Gibco, US) with 1% HT supplement (Cat #:11067-030, Gibco). Cell cultures were kept for 10 days in an incubator with 5% $CO_2$ at 37° C. Cell cultures were collected and subject to centrifugation at 3500 rpm for 5 minutes followed by filtration using a 0.22 µm capsule to remove the cell debris. Monoclonal antibodies were then purified using a pre-equilibrated Protein-A affinity column (Cat #:17040501, GE, US) and eluted with elution buffer (20 mM citric acid, pH3.0-pH3.5). Then, antibodies were kept in PBS buffer (pH 7.0), and their concentrations were determined using a NanoDrop instrument.

The isotype of each purified antibody was determined by using Rapid Isotyping Kit with Kappa and Lambda-Mouse (Cat #:26179, Thermal, US) and Mouse Monoclonal Antibody Isotyping Reagents (Cat #:IS02-1KT, Sigma, US), following the manufacturer's manuals.

Most clones, including 3C2 and 56E5, produced IgG1/kappa antibodies, while the remaining ones produced IgG2a/kappa or IgG2b/kappa antibodies. The expression titers for clone 3C2 and 56E5 were 6.3 mg/L and 7.8 mg/L, respectively.

Example 4. Mouse Anti-PD-L1 Monoclonal Antibodies Bound to Human and Monkey PD-L1s Expressed on HEK293A Cells To determine whether the anti-PD-L1 antibodies bound to human, monkey or mouse PD-L1s expressed on HEK293A cells, a cell-based binding assay was performed by FACS using the HEK293A cells stably overexpressing human, monkey and mouse PD-L1s respectively as generated in Example 1. Briefly, $10^5$ HEK293A cells in 100 µl culture medium were seeded onto each well of the 96-well plates, to which added 50 µl serially diluted anti-PD-L1 antibodies. After incubated at 4° C. for 1 hour, plates were washed 3 times with PBST. Then, APC coupled Goat Anti-Mouse IgG (Cat #:405308, BioLegend, US) diluted 500× was added to the plates. After incubation at 4° C. for 1 hour, the plates were washed with PBS for 3 times and then cell fluorescence was monitored using a FACS machine (BD).

All of the mouse anti-PD-L1 monoclonal antibodies showed high binding capabilities to both human and monkey PD-L1s, but did not bind mouse PD-L1. $EC_{50}$ values of the representative antibodies were summarized in Table 3 below.

TABLE 3

Binding capabilities of mouse anti-PD-L1 antibodies
to human, monkey and mouse PD-L1

| | FACS ($EC_{50}$: M) | | |
|---|---|---|---|
| mAb | HEK293A/human PD-L1 | HEK293A/monkey PD-L1 | HEK293A/mouse PD-L1 |
| 3C2 | 1.75E−9 | 1.25E−9 | No binding |
| 56 E5 | 5.72E−10 | 4.99E−10 | No binding |

Example 5. Epitope Binning

For epitope binning, a competition ELISA assay was performed. Briefly, 96-well plates were coated with 0.5 μg/ml Human PD-L1 (ECD)-His (Cat #:10084-H08H, Sino Biological, CN), 100 μl per well, at 4° C. overnight. The wells were blocked with 200 μl blocking buffer (PBS containing 1% BSA, 1% goat serum and 0.05% Tween 20) for 2 hours at room temperature. Atezolizumab, prepared using the amino acid sequences disclosed in WO2020226986 with human IgG1(N297A)/kappa constant regions, Avelumab, prepared using the amino acid sequences disclosed in WO2013079174A1 with human IgG1/kappa constant regions, Durvalumab, prepared using the amino acid sequences disclosed in US20190276543A1 with human IgG1(L234F, L235E, P331S)/kappa constant regions, and anti-Hel antibody (Cat #:LT12031, LifeTein, US) were respectively diluted to 5 μg/ml, and added to the plates, 100 μl per well. The plates were incubated for 1 hour at room temperature, washed for 3 times with PBST, added with 100 μl 1 μg/ml antibodies of the disclosure, and incubated for 1 hour at room temperature. The ELISA plates were washed for 3 times with PBST, added with anti-mouse Fc-HRP (Cat #:A9309-1MC, Sigma, US) diluted at 1:20000, and incubated for 1 hour at room temperature. Plates were washed by PBST for 3 times, and developed with freshly prepared Ultra-TMB (Cat #:TMB-S-003, Huzhou Yingchuang, CN) for 5 minutes at room temperature. The absorbance was measured in a microplate reader (Thermo Multiscan FC) at 450 nm.

Nine mouse antibodies, including those from clone 3C2, did not compete with atezolizumab, avelumab or durvalumab over epitope binding, indicating that they bound to different epitopes compared to the reference antibodies. The antibodies from clone 56E5 competed with all three reference antibodies over epitope binding, indicating that the 56E5 antibodies bound to same or similar epitopes as the references did.

Example 6. Mouse Anti-PD-L1 Antibodies Inhibited PD-1-PD-L1 Interaction

As reported, PD-1 is the receptor for PD-L1. A cell-based blocking assay was performed by FACS to measure the antibodies' blocking capabilities on PD-1-PD-L1 interaction, using the HEK293A cells stably overexpressing human PD-L1 as generated in Example 1. Briefly, $10^5$ HEK293A/human PD-L1 cells in 100 μl culture medium were seeded onto each well of 96-well plates, to which added 50 μl serially diluted anti-PD-L1 antibodies. After incubated at 4° C. for 1 hour, the plates were washed 3 times with PBST. Then, 200 μg/ml PD1-hFc proteins (Cat #:10377-H02H, Sino Biological, CN) were added into the plates, 100 μl per well. After incubation at 4° C. for 1 hour, the plates were washed with PBST for 3 times, and added with PE coupled Goat Anti-human IgG (Cat #:PAI-86078, Thermofisher, US) diluted 500×. After incubation at 4° C. for 1 hour, the plates were washed with PBST for 3 times and then cell fluorescence was monitored using a FACS machine (BD).

The data showed that only two antibodies were not capable of blocking PD-L1-PD-1 interaction, the remaining eight, including 3C2 and 56E5, blocked PD-L1-PD-1 interaction. $EC_{50}$ values of the representative antibodies were summarized in Table 4

TABLE 4

Blocking capabilities of mouse anti-PD-L1
antibodies on PD-L1-PD-1 interaction

| mAb | PD-L1-PD-1 blocking assay $EC_{50}$(M) |
|---|---|
| Atezolizumab | 1.13E−11 |
| 3C2 | 1.47E−11 |
| 56E5 | 1.00E−11 |

Example 7. Mouse Anti-PDL1 Antibodies Promoted T Cell Activation

The effect of mouse anti-PDL1 antibodies on APC-mediated T cell activation was studied in a mixed lymphocyte reaction (MLR) assay.

Briefly, PBMCs were collected from one healthy human donor's blood sample by density gradient centrifugation, and then re-suspended in RPMI1640 medium. PBMCs were cultured in a 37° C. incubator for 2 hours, and cells adhered to container walls were collected as isolated monocytes. The monocytes were cultured in RPMI1640 medium supplemented with 10% FBS, 100 ng/ml recombinant human GM-CSF (Cat #:7954-GM, R&D, US) and 100 ng/ml recombinant human IL-4 (Cat #:6507-IL, R&D, US). Three days later, half of the medium was replaced with fresh one. On day 6 of culturing, the culture medium was replaced by fresh medium containing 100 ng/ml recombinant human GM-CSF, 100 ng/ml recombinant human IL-4, 10 ng/ml rhTNF-α (Cat #:210-TA-100, R&D, US), 1000 U/ml rhIL-6 (Cat #:7270-IL-025, R&D, US), 1 μg/ml PGE2 (Cat #:363-24-6, TOCRIS, US) and 10 ng/ml IL-1β (Cat #:210-LB-025, R&D, US). The cells were cultured for another 2 days. Then, PBMCs from another healthy human donor's blood sample were collected by density gradient centrifugation and then re-suspended in RPMI1640 medium. CD4$^+$ T cells were isolated from the PBMCs using Invitrogen Dynabeads Untouched Human CD4$^+$ T cells isolation kit (Cat #:11346D, Thermal Fisher Scientific, US), according to the manufacturer's instructions. The dendritic cells from the first donor and the CD4$^+$ T cells from the second donor were seeded on 96 well U-bottom plates respectively at 2.5×10$^4$ cells/well and 5×10$^4$ cells/well, in a total of 150 μl culture medium per well. The plates were added with 50 μl anti-PD-L1 antibodies (0.1-10 μg/ml), or the anti-Hel control (Cat #:LT12031, LifeTein, US), and further incubated for 72 hours. IFN-γ concentration was determined by an ELISA kit (Cat #:SIF50, R&D, US) following the manufacturer's protocol. The assay was done in triplicate.

As shown in FIG. 1(A), highest IFN-γ levels were detected in wells treated with 3C2 and 56E5 antibodies. These antibodies increased IFN-γ secretion by T cells compared to anti-Hel isotype control, in a dose dependent manner (FIG. 1(B)).

Example 8. Expression and Purification of Chimeric Anti-PD-L1 Antibodies

The 3C2 and 56E5 antibodies were further studied. The heavy/light chain variable region sequences of the two antibodies were cloned from hybridoma cells using the standard PCR method with a set of primers as describes in literatures (Juste et al., (2006), *Anal Biochem.* 349(1):159-61), and sequenced. The sequences were summarized in Table 1 and Table 8. Expression vectors were constructed by inserting the sequences encoding the variable region sequences plus human IgG1(N297A)/kappa constant region sequences (amino acid sequences of heavy chain constant region and light chain constant region set forth in SEQ ID NOs: 33 and 34, respectively) into XhoI/BamHI restriction sites of pCDNA3.1 (Invitrogen, Carlsbad, US).

The expression vectors were PEI transfected into HEK-293F cells (Cobioer, N.J., CN). In specific, HEK-293F cells were cultured in Free Style™ 293 Expression Medium (Cat #:12338-018, Gibco) and transfected with the expression vectors using polyethyleneinimine (PEI) at a DNA:PEI ratio of 1:3, 1.5 μg DNAs per millimeter of cell medium. Transfected HEK-293F cells were cultured in an incubator at 37° C. under 5% $CO_2$ with shaking at 120 RPM. After 10-12 days, supernatants were harvested and monoclonal antibodies were purified as described in Example 3.

Example 9. Chimeric Anti-PD-L1 Monoclonal Antibodies Bound to Human and Monkey PD-L1s The chimeric anti-PD-L1 antibodies were further characterized for their abilities of binding to human PD-L1, monkey PD-L1 and mouse PD-L1. Briefly, ELISA plates were coated with 500 ng/ml human PD-L1 (ECD)-his (Cat #:10084-H08H, Sino Biological, CN), 100 μl per well, at 4° C. overnight. The wells were blocked with 200 μl blocking buffer (PBS containing 1% BSA, 1% goat serum and 0.05% Tween 20) for 2 hours at room temperature, added and incubated with 100 μl serially diluted anti-PD-L1 antibodies (starting at 40 μg/ml) for 1 hour at room temperature. The plates were washed for 3 times with PBST (PBS+0.05% Tween 20), added with Goat-anti-human IgG-HRP (Cat #:31410, Thermal, US) diluted 5000×, and incubated for 1 hour at room temperature. Plates were developed with freshly prepared Ultra-TMB (Cat #:555214, BD, US) for 5 minutes at room temperature. Absorbance was read on a SpectraMax® i3X reader (Molecular Devies, US) at 450 nm.

Species-cross-reactivities of the anti-PD-L1 mAbs to monkey or mouse PD-L1s were further assessed by direct ELISA. Briefly, 96-well ELISA plates were coated with 500 ng/ml monkey PD-L1 (ECD)-his (Cat #:90251-C08H, Sino Biological, CN) or mouse PD-L1 (ECD)-his (Cat #:50010-M08H, Sino Biological, CN), 100 μl per well, then added and incubated with 100 μl serially diluted anti-PD-L1 antibodies (starting at 40 μg/ml). The plates were then added and incubated with Goat anti-human IgG conjugated with HRP (Cat #:31410, Thermal, US) for 1 hour at room temperature. Plates were developed with freshly prepared Ultra-TMB (Cat #:555214, BD, US) for 5 minutes at room temperature, and absorbance was read on a SpectraMax® i3X reader (Molecular Devies, US) at 450 nm. Atezolizumab was used as a reference antibody.

The $EC_{50}$ values of the representative antibodies in the binding capability tests were summarized in Table 5. The data showed that all the chimeric antibodies had high binding capabilities to human and monkey PD-L1s, but did not bind mouse PD-L1. The binding capabilities of the chimeric 3C2 and 56E5 antibodies were comparable to those of their parent antibodies and higher than that of atezolizumab.

TABLE 5

Binding capabilities of chimeric anti-PDL1 mAbs to human, monkey and mouse PD-L1

| mAb | ELISA ($EC_{50}$: M) | | |
|---|---|---|---|
| | human PD-L1 (ECD)-his | monkey PD-L1 (ECD)-his | mouse PD-L1-his |
| 3C2 | 4.56E−11 | 1.72E−10 | No binding |
| 56E5 | 3.48E−10 | 2.05E−9 | No binding |
| Atezolizumab | 8.79E−11 | 6.28E−9 | 1.02E−9 |

The antibodies were also tested for their binding capabilities to HEK293A/human PD-L1 cells, HEK293A/monkey PD-L1 cells and HEK293A/mouse PD-L1 cells as generated in Example 1, following the protocol of Example 4. The test results were shown in FIG. 2.

Figure 2:
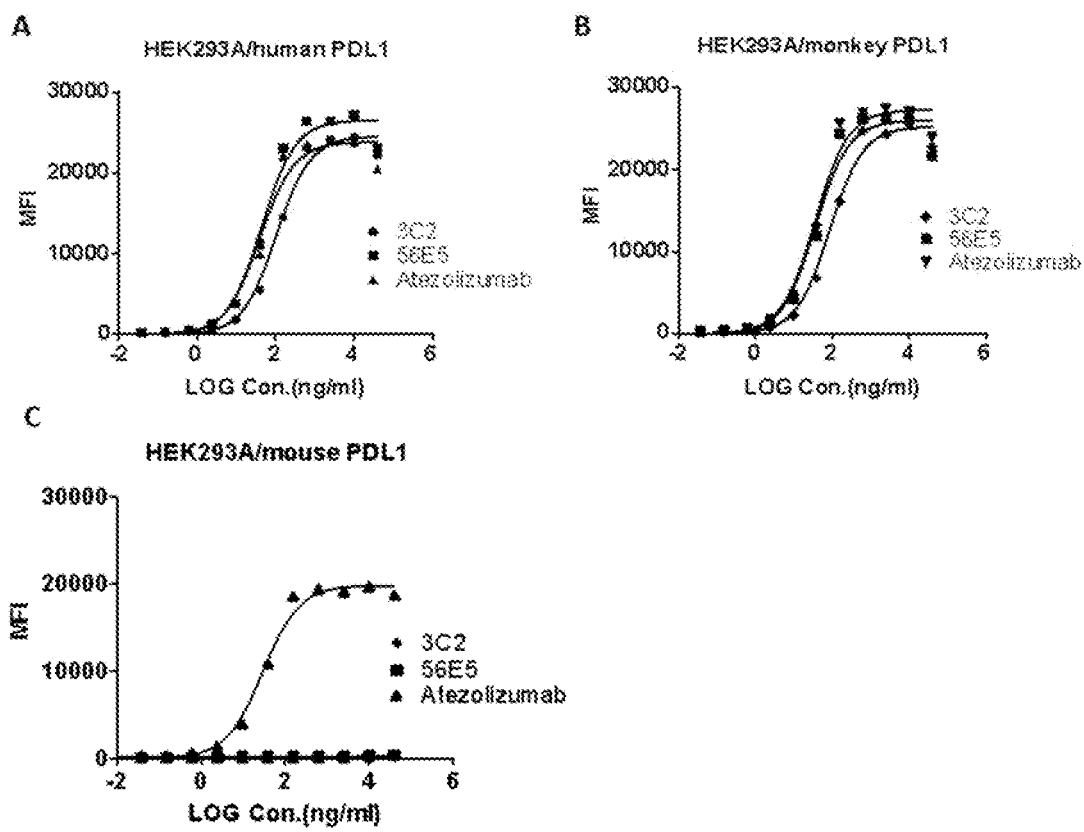
FIG. 2 shows the binding capabilities of chimeric anti-PD-L1 antibodies to HEK293A/human PD-L1 cells (A), HEK293A/monkey PD-L1 cells (B), and HEK293A/mouse PD-L1 cells (C).

As shown in FIG. 2, the chimeric antibodies had high binding capabilities to both human PD-L1 (FIG. 2(A)) and monkey PD-L1 (FIG. 2(B)), but did not bind to mouse PD-L1 (FIG. 2(C)).

Example 10. Chimeric Anti-PD-L1 Monoclonal Antibodies Inhibited PD-L1-PD-1 Interaction The chimeric anti-PD-L1 antibodies were further characterized for their blocking abilities on PD-1-PD-L1 interaction, using the HEK293A/human PD-L1 cells as generated in Example 1, following the protocol of Example 6. The test results were shown in FIG. 3.

Figure 3:
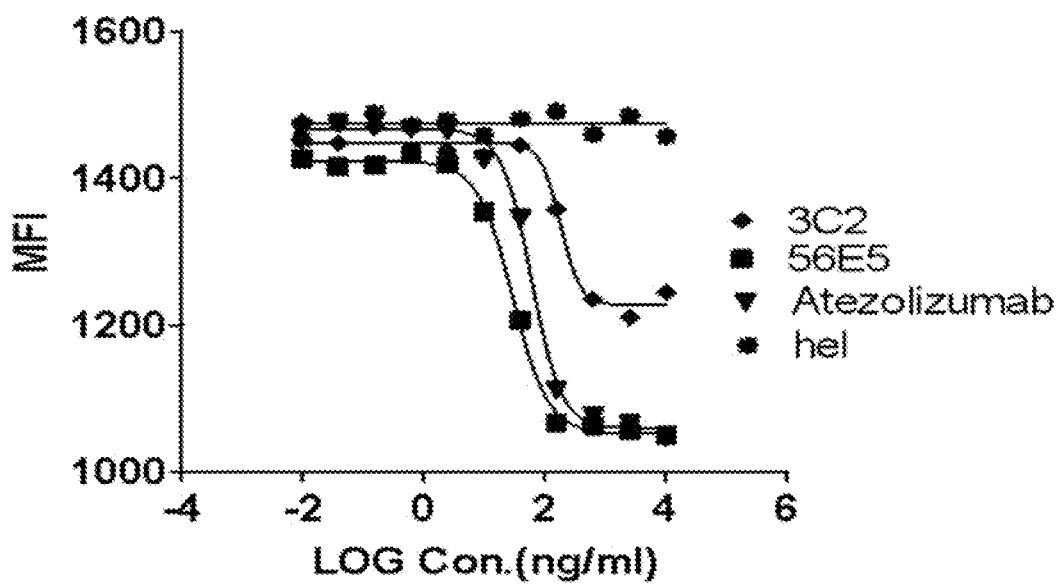
FIG. 3 shows the capabilities of chimeric anti-PD-L1 antibodies to block PD-1-PD-L1 interaction.

According to FIG. 3, the chimeric antibodies evidently blocked PD1-PD-L1 interaction, with chimeric 56E5 showing the best blocking effect, which was better than that of atezolizumab.

Example 11. Chimeric Anti-PD-L1 Monoclonal Antibodies Promoted T Cell Activation These chimeric antibodies were further tested for their abilities to stimulate T cell response in a T cell function assay according to the protocol of Example 7. IFN-γ levels were determined using a commercially available kit (Cat #: STA00C, R&D, US), following the manufacturer's instruction.

Figure 4:
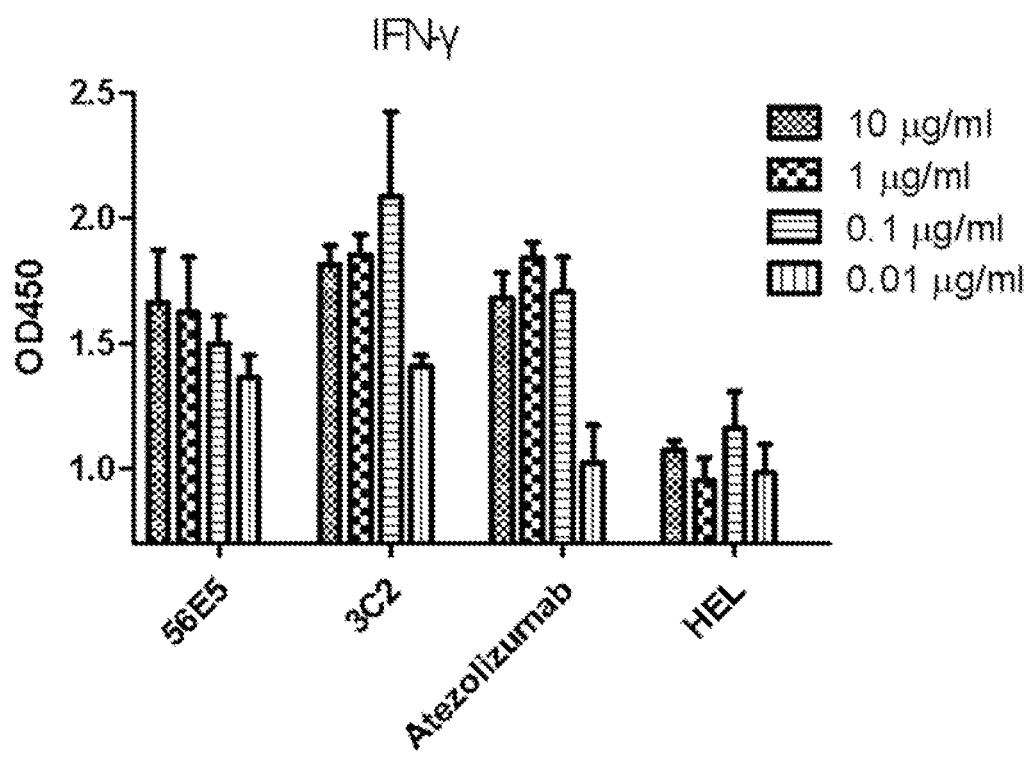
FIG. 4 shows chimeric anti-PD-L1 antibodies induced IFN-γ secretion by T cells in a dose dependent manner.

As shown in FIG. 4, all the tested chimeric antibodies promoted T cell activities, with increased IFN-γ secretion. The chimeric 56E5 antibody was more potent in T cell activation than atezolizumab at a low dose, e.g., 0.01 μg/mL. The chimeric 3C2 antibody's capability in T cell activation was higher than atezolizumab at all test doses.

Example 12. Humanization of Anti-PD-L1 Antibodies

Based on the assays above, 3C2 and 56E5 were humanized and further investigated. Humanization of the murine antibodies was conducted using the well-established CDR-grafting method (U.S. Pat. No. 5,225,539, incorporated herein by reference in its entirety) as described in detail below.

To select acceptor frameworks for humanization of murine antibodies 3C2 and 56E5, the light and heavy chain variable region sequences of 3C2 and 56E5 were blasted against the human immunoglobulin gene database in NCBI website (ncbi.nlm.nih.gov/igblast/). The human germline IGVH and IGVK with the highest homology to 3C2 and 56E5 were selected as the acceptors for humanization. For 3C2, the human heavy chain acceptor selected was IGHV1-46*01, and the human light chain acceptor selected was IGKV1-33*01. For 56E5, the human heavy chain acceptor selected was IGHV4-31*02, and the human light chain acceptor selected was IGKV4-1*01.

The three dimensional structures were simulated for variable domains of 3C2 and 56E5, in order to identify key framework residues that might be playing important roles in supporting CDR loop structures, thus designing back mutations in humanized antibodies.

Based on the structural modeling as described above, 10 potential back-mutations (M48I, M70L, R72V, R87T, R38K, A40R, T28S, Y95F, R67K, V68A) were identified for 3C2's heavy chain and 7 back-mutations (K45R, Y49S, F71Y, T22S, K42N, T85V, F73L) for the light chain. For 56E5, 10 potential back-mutations (S30T, W47Y, I48M, S70T, R87T, K43N, G44K, V71R, V67I, T68S) were identified for the heavy chain, and 4 back-mutations (I21M, R18K, A19V, V89L) were identified for the light chain.

Five humanized heavy chain variable regions and four humanized light chain variable regions were designed for 3C2, with total of 13 humanized antibodies obtained. Four humanized heavy chain variable regions and three humanized light chain variable regions were designed for 56E5, with a total of 12 humanized antibodies obtained. The sequences of these humanized antibodies were summarized in Table 1 and Table 8.

EXPiCHO expression systems (Invitrogen, USA) were transfected with heavy chain and light chain expressing vectors and transiently expressed 25 humanized anti-PD-L1 antibodies, following the protocol described in Example 8. The humanized antibodies were purified as described in Example 3.

Example 13. Binging Capabilities/Affinities of Humanized Anti-PD-L1 Antibodies

The humanized anti-PD-L1 antibodies were characterized for their binding abilities to HEK293A/human PD-L1 cells, HEK293A/monkey PD-L1 cells and HEK293A/mouse PD-L1 cells, following the protocols described in Example 4. The results were shown in FIG. 5 and FIG. 6.

These antibodies were also tested in SPR assays for their binding affinities to human and monkey PD-L1 with BIAcore™ 8K instrument (GE Life Sciences). Briefly, 100-200 response units (RU) of human PD-L1 (ECD)-his protein (Cat #:10084-H08H, Sino Biological, CN) or monkey PD-L1 (ECD)-his protein (Cat #:90251-008H, Sino Biological, CN) were coupled to CM5 biosensor chips (Cat #:BR-1005-30, GE Life Sciences, US), and the un-reacted groups were blocked with 1M ethanolamine Serially diluted antibodies at concentrations ranging from 0.3 μM to 10 μM were injected into the SPR running buffer (HBS-EP buffer, pH7.4, Cat #:BR-1006-69, GE Life Sciences, US) at 30 μL/minute. The binding affinities were calculated with the RUs of blank controls subtracted. The association rate ($k_a$) and dissociation rate ($k_d$) were calculated using the one-to-one Langmuir binding model (BIA Evaluation Software, GE Life Sci-

TABLE 6

Back mutations

| Heavy chain | Back mutations | Light chain | Back mutations |
| --- | --- | --- | --- |
| 3C2VH2 | M48I, M70L, R72V, R87T | 3C2VL2 | K45R, Y49S, F71Y |
| 3C2VH3 | M48I, M70L, R72V, R87T, R38K, A40R | 3C2VL3 | K45R, Y49S, F71Y, T22S, K42N |
| 3C2VH4 | M48I, M70L, R72V, R87T, R38K, A40R, T28S, Y95F | 3C2VL4 | K45R, Y49S, F71Y, T22S, K42N, T85V |
| 3C2VH5 | M48I, M70L, R72V, R87T, R38K, A40R, T28S, Y95F, R67K, V68A | 3C2VL5 | Y49S, F73L |
| 3C2VH6 | R72V, M48I | | |
| 56E5VH2 | S30T, W47Y, I48M, S70T, R87T | 56E5VL2 | I21M |
| 56E5VH3 | S30T, W47Y, I48M, S70T, R87T, K43N, G44K | 56E5VL3 | I21M, R18K, A19V |
| 56E5VH4 | S30T, W47Y, I48M, S70T, R87T, K43N, G44K, V71R | 56E5VL4 | I21M, R18K, A19V, V89L |
| 56E5VH5 | S30T, W47Y, I48M, S70T, R87T, K43N, G44K, V71R, V67I, T68S | | |

The sequences encoding the heavy chain variable region plus human IgG1 constant region with N297A mutation and the sequences encoding the light chain variable regions plus human kappa constant region (amino acid sequences of heavy chain constant region and light chain constant region set forth in SEQ ID NOs: 33 and 34, respectively) were chemically synthesized and then subcloned into GS expression vectors (Invitrogen, USA) using the EcoR I/Xho I and Cla I/Hind III restriction sites respectively. All expression constructs were confirmed by DNA sequencing. The ences), and the equilibrium dissociation constant $K_D$ was calculated as the $k_d/k_a$ ratio. The results were shown in Table 7.

Figure 5:
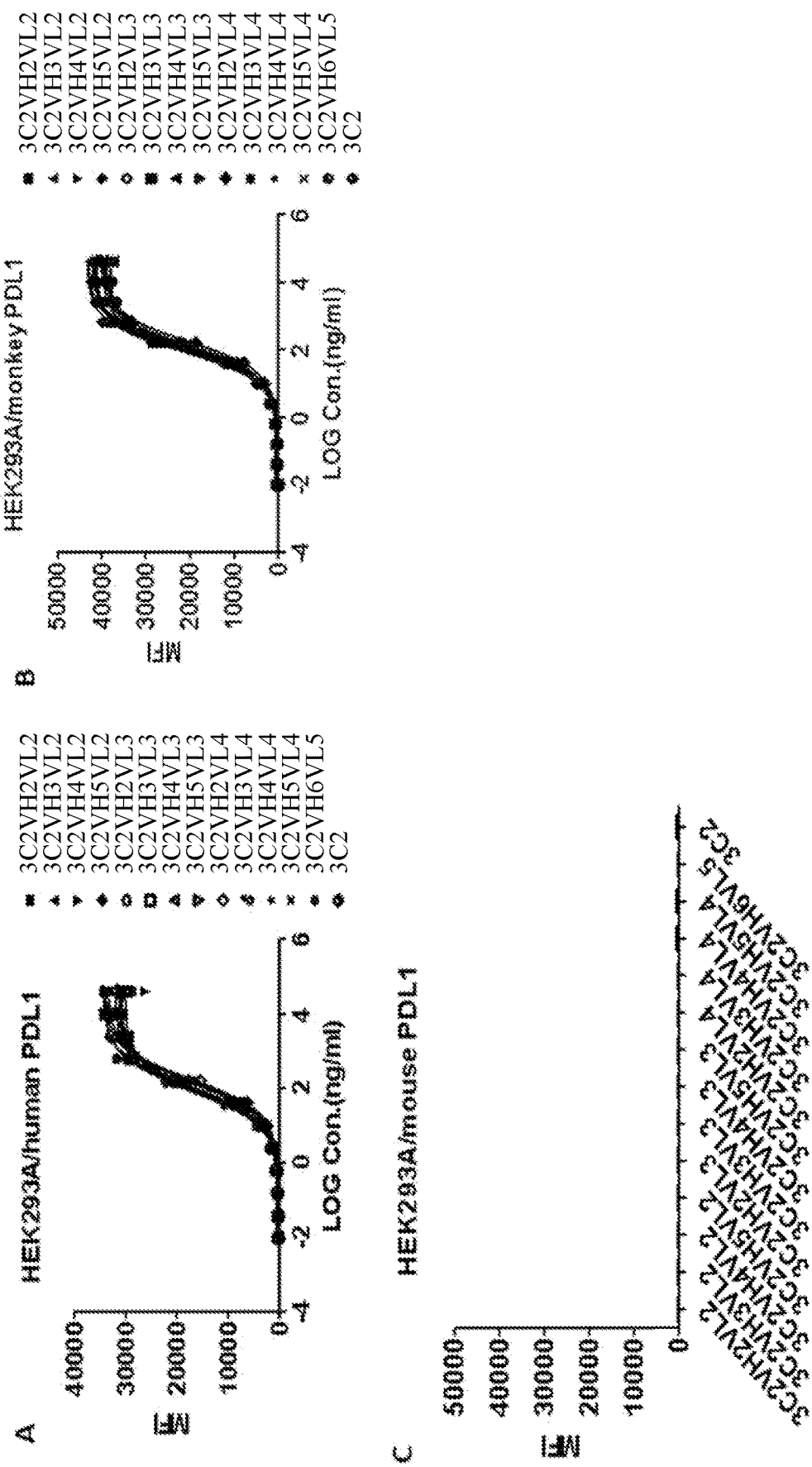
FIG. 5 shows the binding capabilities of humanized 3C2 antibodies to HEK293A/human PD-L1 cells (A), HEK293A/monkey PD-L1 cells (B), and HEK293A/mouse PD-L1 cells (C).
Figure 6:
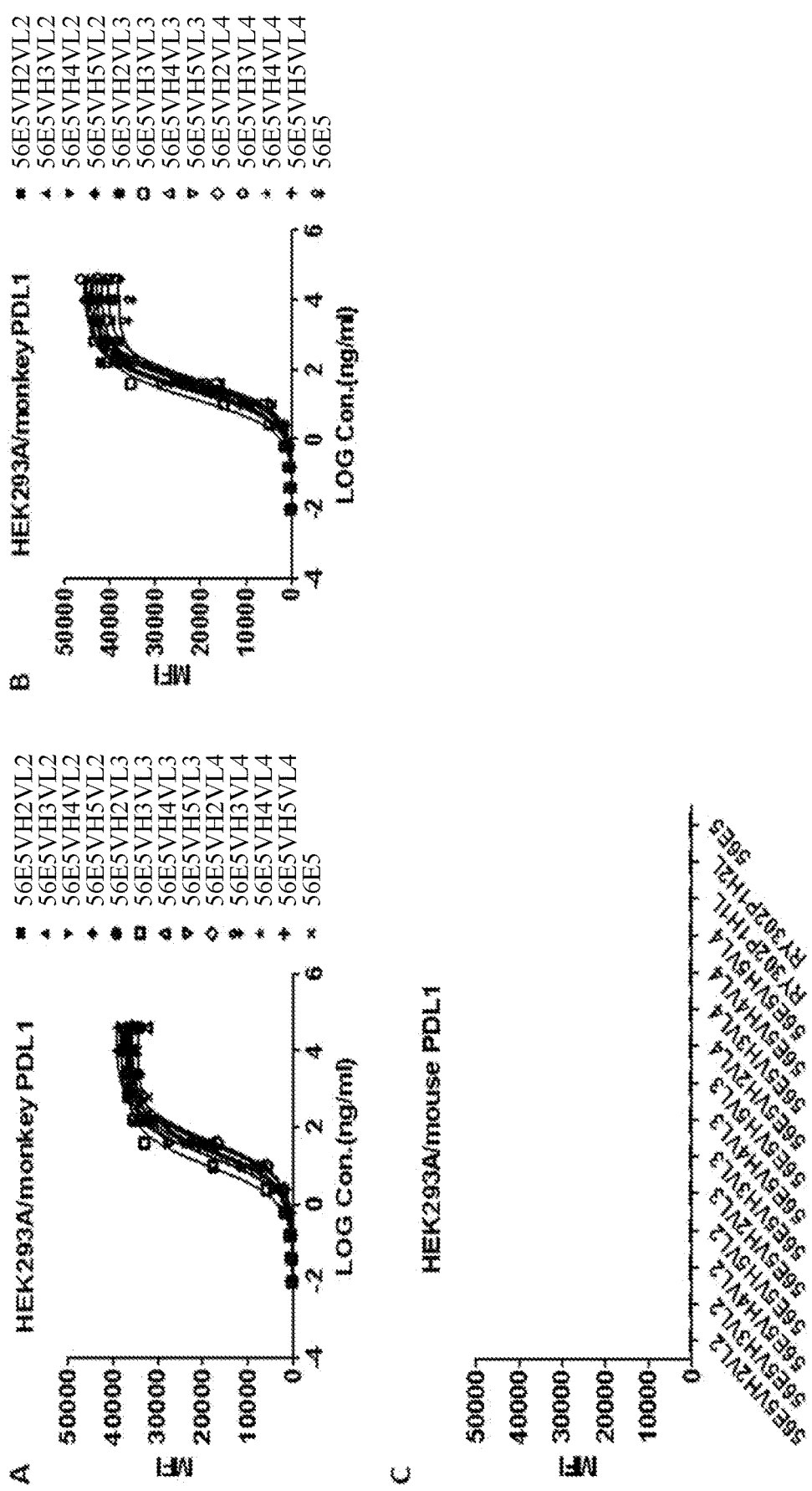
FIG. 6 shows the binding capabilities of humanized 56E5 antibodies to HEK293A/human PD-L1 cells (A), HEK293A/monkey PD-L1 cells (B), and HEK293A/mouse PD-L1 cells (C).

As shown in FIG. 5 and FIG. 6, the humanized anti-PDL1 antibodies had high binding abilities to both human PD-L1 and monkey PD-L1, which were comparable to those of their respective chimeric antibodies.

According to Table 7, the humanized 3C2 and 56E5 antibodies had comparable or higher binding affinities to human PD-L1 as compared to atezolizumab.

TABLE 7

Binding affinities of humanized anti-PDL1 antibodies to human/monkey PD-L1

| mAb | Human PD-L1 | | | Monkey PD-L1 | | |
|---|---|---|---|---|---|---|
| | $K_a$ | $K_d$ | $K_D$ | $K_a$ | $K_d$ | $K_D$ |
| 3C2VH4VL4 | 3.16e+05 | 9.69e−05 | 3.07e−10 | 3.16e+05 | 7.75e−05 | 2.45e−10 |
| 3C2VH6VL5 | 2.77e+05 | 1.20e−04 | 4.33e−10 | 4.16e+05 | 1.53e−04 | 3.69e−10 |
| 56E5VH5VL3 | 1.04e+06 | 3.19e−05 | 3.08e−11 | 2.49e+05 | 1.10e−04 | 4.41e−10 |
| 56E5VH5VL4 | 2.07e+05 | 1.07e−04 | 5.18e−10 | 8.16e+05 | 6.58e−06 | 8.07e−12 |
| Atezolizumab | 4.77e+05 | 5.88e−05 | 1.23e−10 | 1.92e+05 | 1.25e−04 | 6.50e−10 |

Example 14. Humanized Anti-PD-L1 Antibodies Activated T Cells

These antibodies were further tested for their abilities to stimulate T cell response in a MLR assay, following the protocol of Example 7. IFN-γ levels were determined using a commercially available kit (Cat #:STA00C, R&D, US) following the manufacturer's instructions.

Figure 7:
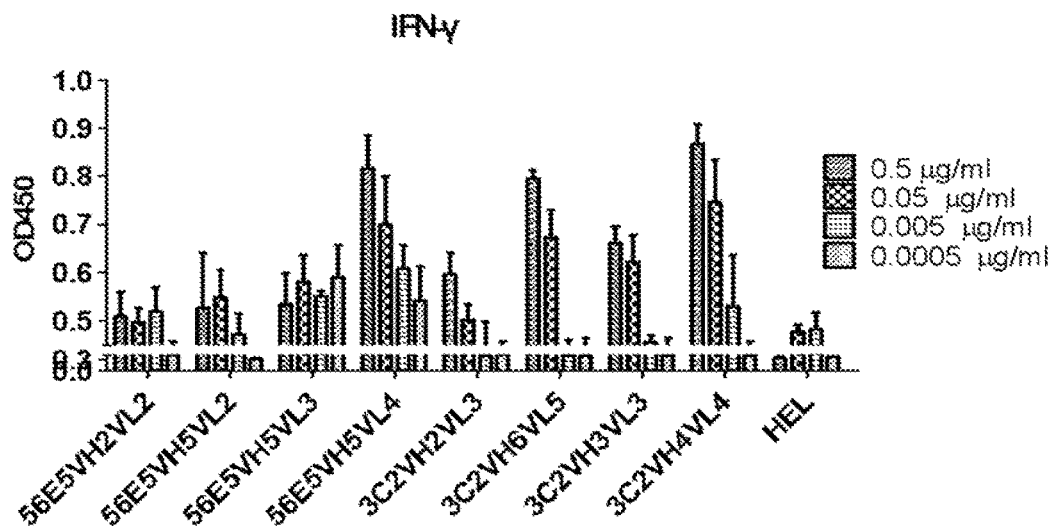
FIG. 7 shows humanized 56E5 and 3C2 antibodies induced IFN-γ secretion by T cells in a dose dependent manner.
Figure 8:
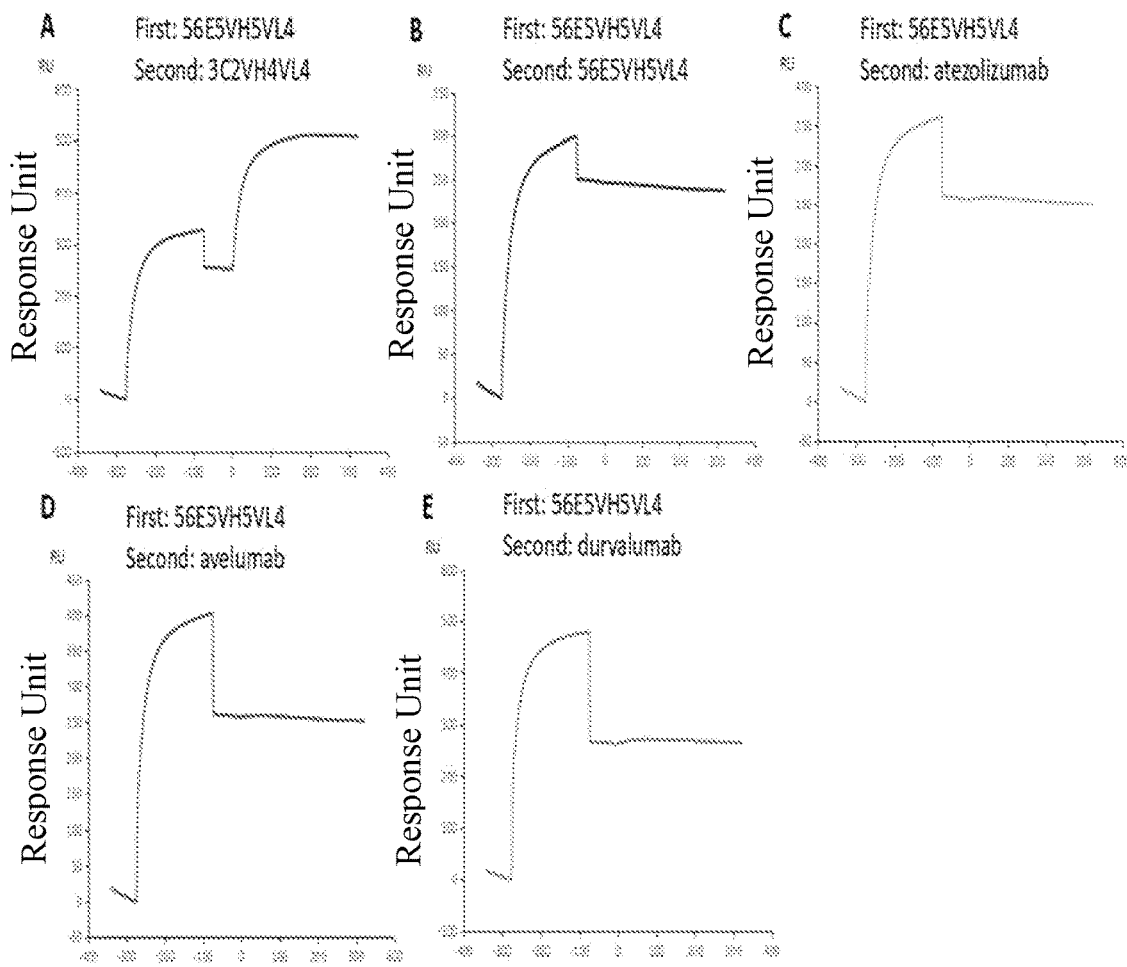
FIG. 8 shows the SPR curves of the anti-PDL1 antibody 56E5VH5VL4 in competition with 3C2VH4VL4 (A), 56E5VH5VL4 (B), Atezolizumab (C), Avelumab (D) and Duralumab (E) over PD-L1 binding.
Figure 9:
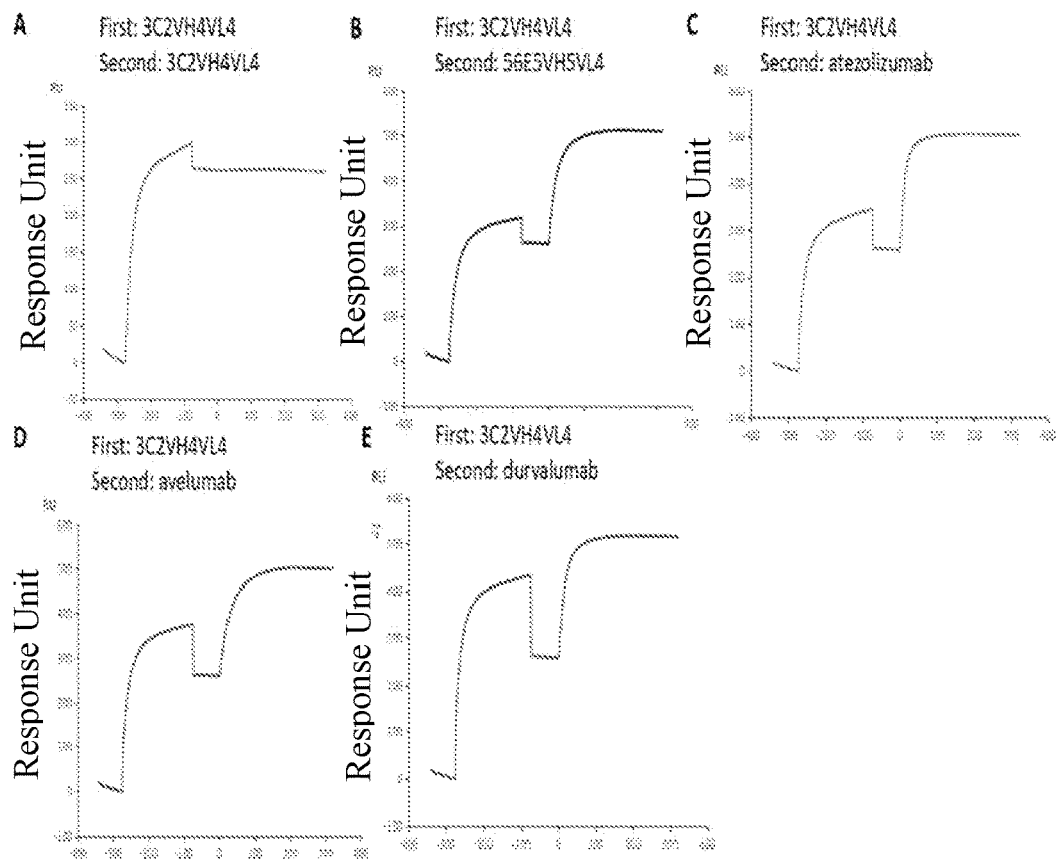
FIG. 9 shows the SPR curves of the anti-PDL1 antibody 3C2VH4VL4 in competition with 3C2VH4VL4 (A), 56E5VH5VL4 (B), Atezolizumab (C), Avelumab (D) and Duralumab (E) over PD-L1 binding.

As shown in FIG. 7, all humanized antibodies promoted T cell activation in a dose dependent manner, with increased IFN-γ secretion. Antibodies 56E5VH5VL4 and 3C2VH4VL4 showed the highest capabilities in T cell activation.

Example 15. Epitope Binning

For epitope binning, a competition SPR assay was performed. Briefly, 1 μg/ml human PD-L1 (ECD)-his protein (Cat #:10084-H08H, Sino Biological, CN) was coupled to CM5 biosensor chips (Cat #:BR-1005-30, GE Life Sciences, US), and un-reacted groups were blocked with 1 M ethanolamine. Then, 5 μg/ml 56E5VH5VL4 or 3C2VH4VL4 antibodies were injected into the SPR running buffer (HBS-EP buffer, pH7.4, Cat #:BR-1006-69, GE Life Sciences, US) at 30 μL/minute, followed by a second anti-PDL1 antibody (56E5VH5VL4, 3C2VH4VL4, atezolizumab, avelumab or durvalumab), 5 μg/ml, at 30 μL/minute. The binding affinities were calculated with the RUs of blank controls subtracted. The data were then fitted using a 1:1 interaction model.

As shown in FIG. 8 and FIG. 9, 56E5VH5VL4 and atezolizumab did not bind the PD-L1 molecules at the same time, suggesting they may bind to the same or similar epitopes. Similarly, 56E5VH5VL4 competed with avelumab and furvalumab over epitope binding. While 56E5VH5VL4 and 3C2VH4VL4 simultaneously bound to the PD-L1 molecules, meaning they bound to different epitopes. The antibody 3C2VH4VL4 bound to the PD-L1 molecules simultaneously with 56E5VH5VL4, atezolizumab, avelumab or furvalumab, suggesting that 3C2VH4VL4 may bind to a novel epitope different from those bound by the other antibodies.

Example 16. Humanized Anti-PDL1 Antibodies had In Vivo Anti-Tumor Effect

In vivo anti-tumor activities of anti-PD-L1 antibodies 56E5VH5VL4 and 3C2VH6VL5 having human IgG1 (N297A)/kappa constant regions were studied in an animal model established by grafting MC38 murine colon adenocarcinoma in transgenic mice with human PD-L1 (GemPharmatech Co. Ltd, China). On Day 0, mice were subcutaneously injected with $1\times10^6$ MC38 cells at one flank, and randomly allocated into 7 groups, 8 mice per group. These animals were then intraperitoneally administered with 56E5VH5VL4 (10 mg/kg), 3C2VH6VL5 (10 mg/kg), avelumab (10 mg/kg) and PBS respectively at Day 0, 4, 7, 11, 14 and 18.

Tumor sizes and mice body weights were monitored over time. In specific, the tumor size was determined by measuring by a caliper the length (the longest diameter) and width (the diameter perpendicular to the length) of a tumor and calculating the tumor volume as $0.5\times D\times d^2$. The test was terminated before the tumor sizes in the control group reached 3.5 cm³. One-way ANOVA was used to identify tumor size differences among groups.

Figure 10:
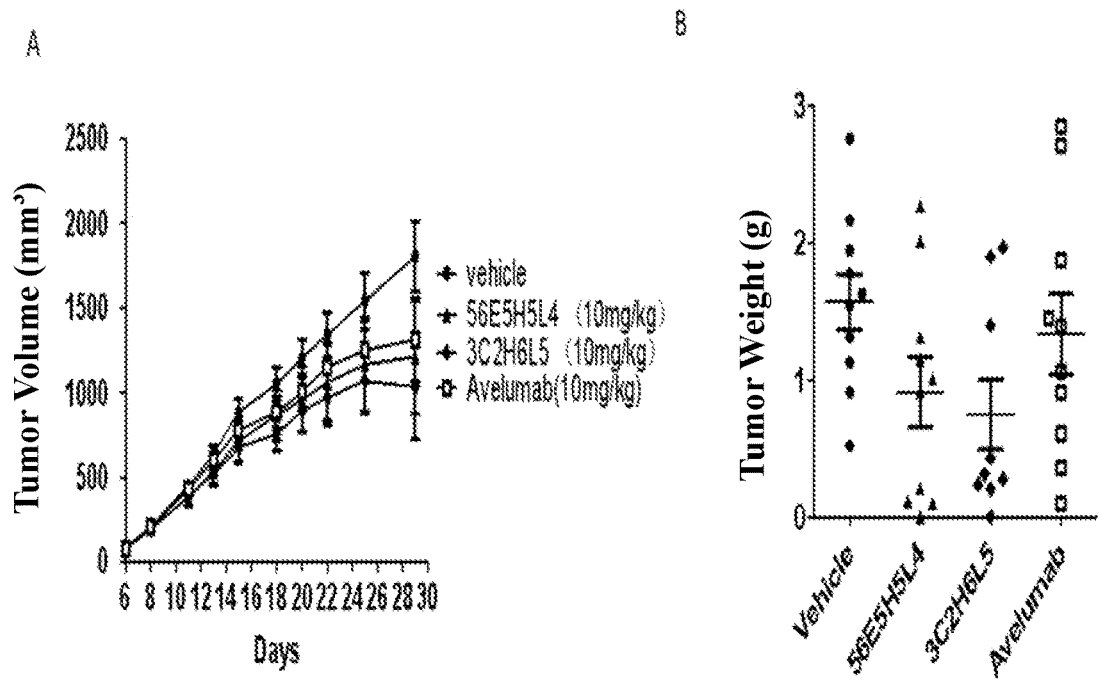
FIG. 10 shows the average tumor volumes (A) and average tumor weights (B) of transgenic mice with human PD-L1 in groups respectively treated with 56E5VH5VL4, 3C2VH6VL5 and Avelumab.

As shown in FIG. 10, all the anti-PD-L1 antibodies significantly inhibited tumor growth in mice, with 56E5VH5VL4 and $3C2V_H6VL5$'s anti-tumor effects better than that of avelumab.

The sequences in the application are summarized as follows in Table 8.

TABLE 8

Sequences

```
Description/
Sequence/SEQ ID NO.

VH-CDR1 of mouse, chimeric and humanized 3C2 antibodies
DYHVN (SEQ ID NO: 1)

VH-CDR2 of mouse, chimeric and humanized 3C2 antibodies
WIFPGSGRTFYTDKFKG (SEQ ID NO: 2)

VH-CDR3 of mouse, chimeric and humanized 3C2 antibodies
DYGTSGYGLVY (SEQ ID NO: 3)

VL-CDR1 of mouse, chimeric and humanized 3C2 antibodies
KASDRINNWLA (SEQ ID NO: 4)
```

TABLE 8-continued

Sequences

Description/
Sequence/SEQ ID NO.

VL-CDR2 of mouse, chimeric and humanized 3C2 antibodies
GATSLET (SEQ ID NO: 5)

VL-CDR3 of mouse, chimeric and humanized 3C2 antibodies
QQYWNIPFT (SEQ ID NO: 6)

VH-CDR1 of mouse, chimeric and humanized 56E5 antibodies
SDYWN (SEQ ID NO: 7)

VH-CDR2 of mouse, chimeric and humanized 56E5 antibodies
YISYTGSTYYNPSLKS (SEQ ID NO: 8)

VH-CDR3 of mouse, chimeric and humanized 56E5 antibodies
YRDWDVRAMDY (SEQ ID NO: 9)

VL-CDR1 of mouse, chimeric and humanized 56E5 antibodies
KSSQSLLISGNQKNFLT (SEQ ID NO: 10)

VL-CDR2 of mouse, chimeric and humanized 56E5 antibodies
WASTRES (SEQ ID NO: 11)

VL-CDR3 of mouse, chimeric and humanized 56E5 antibodies
QNDFGFPFT (SEQ ID NO: 12)

VH of mouse and chimeric 3C2 antibodies
QVQLNQSGPELMKAGTSVKISCKASGYSFTDYHVNWVKQRPGQGLEWIGWIFPGSGRTFYTDK
FKGKATLTVDLSFTTAYIMLNSLTSEDSAVYFCATDYGTSGYGLVYWGQGTSVTVSS (SEQ ID
NO: 13)

VH of humanized antibodies 3C2-VH2VL2, 3C2-VH2VL3 and 3C2-VH2VL4
QVQLVQSGAEVKKPGASVKVSCKASGYTFTDYHVNWVRQAPGQGLEWIGWIFPGSGRTFYTDK
FKGRVTLTVDTSTSTVYMELSSLTSEDTAVYYCATDYGTSGYGLVYWGQGTTVTVSS (SEQ ID
NO: 14)

VH of humanized antibodies 3C2-VH3VL2, 3C2-VH3VL3 and 3C2-VH3VL4
QVQLVQSGAEVKKPGASVKVSCKASGYTFTDYHVNWVKQRPGQGLEWIGWIFPGSGRTFYTDK
FKGRVTLTVDTSTSTVYMELSSLTSEDTAVYYCATDYGTSGYGLVYWGQGTTVTVSS (SEQ ID
NO: 15)

VH of humanized antibodies 3C2-VH4VL2, 3C2-VH4VL3 and 3C2-VH4VL4
QVQLVQSGAEVKKPGASVKVSCKASGYSFTDYHVNWVKQRPGQGLEWIGWIFPGSGRTFYTDK
FKGRVTLTVDTSTSTVYMELSSLTSEDTAVYFCATDYGTSGYGLVYWGQGTTVTVSS (SEQ ID
NO: 16)

VH of humanized antibodies 3C2-VH5VL2, 3C2-VH5VL3 and 3C2-VH5VL4
QVQLVQSGAEVKKPGASVKVSCKASGYSFTDYHVNWVKQRPGQGLEWIGWIFPGSGRTFYTDK
FKGKATLTVDTSTSTVYMELSSLTSEDTAVYFCATDYGTSGYGLVYWGQGTTVTVSS (SEQ ID
NO: 17)

VH of humanized antibody 3C2-VH6VL5
QVQLVQSGAEVKKPGASVKVSCKASGYTFTDYHVNWVRQAPGQGLEWIGWIFPGSGRTFYTDK
FKGRVTMTVDTSTSTVYMELSSLRSEDTAVYYCATDYGTSGYGLVYWGQGTTVTVSS (SEQ ID
NO: 18)

VH of mouse and chimeric 56E5 antibodies
EVQLQESGPGLAKPSQTLSLTCSVTGYSITSDYWNWIRKFPGNKLEYMGYISYTGSTYYNPSLKS
RISITRDTSKNQYYLQLNSVTTEDTATYYCARYRDWDVRAMDYWGQGTSVTVSS (SEQ ID NO:
19)

VH of humanized antibodies 56E5-VH2VL2, 56E5-VH2VL3 and 56E5-VH2VL4
QVQLQESGPGLVKPSQTLSLTCTVSGGSITSDYWNWIRQHPGKGLEYMGYISYTGSTYYNPSLKS
RVTITVDTSKNQFSLKLSSVTTADTAVYYCARYRDWDVRAMDYWGQGTTVTVSS (SEQ ID
NO: 20)

VH of humanized antibodies 56E5-VH3VL2, 56E5-VH3VL3 and 56E5-VH3VL4
QVQLQESGPGLVKPSQTLSLTCTVSGGSITSDYWNWIRQHPGNKLEYMGYISYTGSTYYNPSLKS
RVTITVDTSKNQFSLKLSSVTTADTAVYYCARYRDWDVRAMDYWGQGTTVTVSS (SEQ ID NO:
21)

VH of humanized antibodies 56E5-VH4VL2, 56E5-VH4VL3 and 56E5-VH4VL4
QVQLQESGPGLVKPSQTLSLTCTVSGGSITSDYWNWIRQHPGNKLEYMGYISYTGSTYYNPSLKS
RVTITRDTSKNQFSLKLSSVTTADTAVYYCARYRDWDVRAMDYWGQGTTVTVSS (SEQ ID NO:
22)

TABLE 8-continued

Sequences

Description/
Sequence/SEQ ID NO.

VH of humanized antibodies 56E5-VH5VL2, 56E5-VH5VL3 and 56E5-VH5VL4
QVQLQESGPGLVKPSQTLSLTCTVSGGSITSDYWNWIRQHPGNKLEYMGYISYTGSTYYNPSLKS
RISITRDTSKNQFSLKLSSVTTADTAVYYCARYRDWDVRAMDYWGQGTTVTSS (SEQ ID NO:
23)

VL of mouse and chimeric 3C2 antibodies
DIQMTQSSSYLSVSLGGRVTISCKASDRINNWLAWYQQKPGNAPRLLISGATSLETGVPSRFSGS
GSGKDYTLSITSLQTEDVAVYYCQQYWNIPFTFGSGTKLEIK (SEQ ID NO: 24)

VL of humanized antibodies 3C2-VH2VL2, 3C2-VH3VL2, 3C2-VH4VL2 and 3C2-VH5VL2
DIQMTQSPSSLSASVGDRVTITCKASDRINNWLAWYQQKPGKAPRLLISGATSLETGVPSRFSGS
GSGTDYTFTISSLQPEDIATYYCQQYWNIPFTFGQGTKVEIK(SEQ ID NO:25)

VL of humanized antibodies 3C2-VH2VL3, 3C2-VH3VL3, 3C2-VH4VL3 and 3C2-VH5VL3
DIQMTQSPSSLSASVGDRVTISCKASDRINNWLAWYQQKPGNAPRLLISGATSLETGVPSRFSGSG
SGTDYTFTISSLQPEDIATYYCQQYWNIPFTFGQGTKVEIK (SEQ ID NO: 26)

VL of humanized antibodies 3C2-VH2VL4, 3C2-VH3VL4, 3C2-VH4VL4 and 3C2-VH5VL4
DIQMTQSPSSLSASVGDRVTISCKASDRINNWLAWYQQKPGNAPRLLISGATSLETGVPSRFSGSG
SGTDYTFTISSLQPEDIAVYYCQQYWNIPFTFGQGTKVEIK (SEQ ID NO: 27)

VL of humanized antibody 3C2-VH6VL5
DIQMTQSPSSLSASVGDRVTITCKASDRINNWLAWYQQKPGKAPKLLISGATSLETGVPSRFSGS
GSGTDFTLTISSLQPEDIATYYCQQYWNIPFTFGQGTKVEIK (SEQ ID NO: 28)

VL of mouse and chimeric 56E5 antibodies
DIVMTQSPSSLTVTAGEKVTMNCKSSQSLLISGNQKNFLTWYQQKPGQPPKLLIYWASTRESGVP
DRFTGSGSGTDFTLTISSVQAEDLAVYYCQNDFGFPFTFGSGTKLEIK(SEQ ID NO: 29)

VL of humanized antibodies 56E5-VH2VL2, 56E5-VH3VL2, 56E5-VH4VL2 and 56E5-VH5VL2
DIVMTQSPDSLAVSLGERATMNCKSSQSLLISGNQKNFLTWYQQKPGQPPKLLIYWASTRESGVP
DRFSGSGSGTDFTLTISSLQAEDVAVYYCQNDFGFPFTFGQGTKVEIK (SEQ ID NO: 30)

VL of humanized antibodies 56E5-VH2VL3, 56E5-VH3VL3, 56E5-VH4VL3 and 56E5-VH5VL3
DIVMTQSPDSLAVSLGEKVTMNCKSSQSLLISGNQKNFLTWYQQKPGQPPKLLIYWASTRESGVP
DRFSGSGSGTDFTLTISSLQAEDVAVYYCQNDFGFPFTFGQGTKVEIK (SEQ ID NO: 31)

VL of humanized antibodies 56E5-VH2VL4, 56E5-VH3VL4, 56E5-VH4VL4 and 56E5-VH5VL4
DIVMTQSPDSLAVSLGEKVTMNCKSSQSLLISGNQKNFLTWYQQKPGQPPKLLIYWASTRESGVP
DRFSGSGSGTDFTLTISSLQAEDVAVYYCQNDFGFPFTFGQGTKVEIK (SEQ ID NO: 32)

Human IgG1 heavy chain constant region (N297A)
ASTKGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFPPKPK
DTLMISRTPEVTCVVVDVSHEDPEVKFNWYVDGVEVHNAKTKPREEQYASTYRVVSVLTVLHQ
DWLNGKEYKCKVSNKALPAPIEKTISKAKGQPREPQVYTLPPSREEMTKNQVSLTCLVKGFYPS
DIAVEWESNGQPENNYKTTPPVLDSDGSFFLYSKLTVDKSRWQQGNVFSCSVMHEALHNHYTQ
KSLSLSPGK (SEQ ID NO: 33)

Human kappa light chain constant region
RTVAAPSVFIFPPSDEQLKSGTASVVCLLNNFYPREAKVQWKVDNALQSGNSQESVTEQDSKDS
TYSLSSTLTLSKADYEKHKVYACEVTHQGLSSPVTKSFNRGEC (SEQ ID NO: 34)

Human PD-L1
MRIFAVFIFMTYWHLLNAFTVTVPKDLYVVEYGSNMTIECKFPVEKQLDLAALIVYWEMEDKNI
IQFVHGEEDLKVQHSSYRQRARLLKDQLSLGNAALQITDVKLQDAGVYRCMISYGGADYKRITV
KVNAPYNKINQRILVVDPVTSEHELTCQAEGYPKAEVIWTSSDHQVLSGKTTTTNSKREEKLFNV
TSTLRINTTTNEIFYCTFRRLDPEENHTAELVIPELPLAHPPNERTHLVILGAILLCLGVALTFIFRLR
KGRMMDVKKCGIQDTNSKKQSDTHLEET (SEQ ID NO: 35)

Monkey PD-L1
MRIFAVFIFTIYWHLLNAFTVTVPKDLYVVEYGSNMTIECKFPVEKQLDLTSLIVYWEMEDKNIIQ
FVHGEEDLKVQHSNYRQRAQLLKDQLSLGNAALRITDVKLQDAGVYRCMISYGGADYKRITVK
VNAPYNKINQRILVVDPVTSEHELTCQAEGYPKAEVIWTSSDHQVLSGKTTTTNSKREEKLLNVT
STLRINTTANEIFYCIFRRLDPEENHTAELVIPELPLALPPNERTHLVILGAIFLLLGVALTFIFYLRK
GRMMDMKKCGIRVTNSKKQRDTQLEET (SEQ ID NO: 36)

Mouse PD-L1
MRIFAGIIFTACCHLLRAFTITAPKDLYVVEYGSNVTMECRFPVERELDLLALVVYWEKEDEQVI
QFVAGEEDLKPQHSNFRGRASLPKDQLLKGNAALQITDVKLQDAGVYCCIISYGGADYKRITLK
VNAPYRKINQRISVDPATSEHELICQAEGYPEAEVIWTNSDHQPVSGKRSVTTSRTEGMLLNVTS
SLRVNATANDVFYCTFWRSQPGQNHTAELIIPELPATHPPQNRTHWVLLGSILLFLIVVSTVLLFL
RKQVRMLDVEKCGVEDTSSKNRNDTQFEET (SEQ ID NO: 37)

Having thus described in detail preferred embodiments of the present disclosure, it is to be understood that the disclosure defined by the above paragraphs is not to be limited to particular details set forth in the above description as many apparent variations thereof are possible without departing from the spirit or scope of the present disclosure.

We claim:

1. An isolated monoclonal antibody, or an antigen-binding portion thereof, binding to PD-L1, comprising a heavy chain variable region comprising a VH-CDR1 region, a VH-CDR2 region and a VH-CDR3 region, and a light chain variable region comprising a VL-CDR1 region, a VL-CDR2 region and a VL-CDR3 region, wherein the VH-CDR1 region, the VH-CDR2 region, the VH-CDR3 region, the VL-CDR1 region, the VL-CDR2 region and the VL-CDR3 region comprise amino acid sequences of (1) SEQ ID NOs: 1, 2, 3, 4, 5 and 6, respectively; or (2) SEQ ID NOs: 7, 8, 9, 10, 11 and 12, respectively.

2. The isolated monoclonal antibody, or the antigen-binding portion thereof, according to claim 1, wherein the heavy chain variable region comprises an amino acid sequence having at least 95% identity to any one of SEQ ID NOs: 13-23.

3. The isolated monoclonal antibody, or the antigen-binding portion thereof, according to claim 1, wherein the light chain variable region comprises an amino acid sequence having at least 95% identity to any one of SEQ ID NO: 24-32.

4. The isolated monoclonal antibody, or the antigen-binding portion thereof, according to claim 2, wherein the heavy chain variable region and the light chain variable region comprise amino acid sequences having at least 95% identity to (1) SEQ ID NOs: 13 and 24, respectively; (2) SEQ ID NOs: 14 and 25, respectively; (3) SEQ ID NOs: 14 and 26, respectively; (4) SEQ ID NOs: 14 and 27, respectively; (5) SEQ ID NOs: 15 and 25, respectively; (6) SEQ ID NOs: 15 and 26, respectively; (7) SEQ ID NOs: 15 and 27, respectively; (8) SEQ ID NOs: 16 and 25, respectively; (9) SEQ ID NOs: 16 and 26, respectively; (10) SEQ ID NOs: 16 and 27, respectively; (11) SEQ ID NOs: 17 and 25, respectively; (12) SEQ ID NOs: 17 and 26, respectively; (13) SEQ ID NOs: 17 and 27, respectively; (14) SEQ ID NOs: 18 and 28, respectively; (15) SEQ ID NOs: 19 and 29, respectively; (16) SEQ ID NOs: 20 and 30, respectively; (17) SEQ ID NOs: 20 and 31, respectively; (18) SEQ ID NOs: 20 and 32, respectively; (19) SEQ ID NOs: 21 and 30, respectively; (20) SEQ ID NOs: 21 and 31, respectively; (21) SEQ ID NOs: 21 and 32, respectively; (22) SEQ ID NOs: 22 and 30, respectively; (23) SEQ ID NOs: 22 and 31, respectively; (24) SEQ ID NOs: 22 and 32, respectively; (25) SEQ ID NOs: 23 and 30, respectively; (26) SEQ ID NOs: 23 and 31, respectively; or (27) SEQ ID NOs: 23 and 32, respectively.

5. The isolated monoclonal antibody, or the antigen-binding portion thereof, according to claim 1, comprising a heavy chain constant region, linked to the heavy chain variable region, having an amino acid sequence having at least 95% identity to SEQ ID NO: 33, and/or a light chain constant region, linked to the light chain variable region, having an amino acid sequence having at least 95% identity to SEQ ID NO: 34.

6. The isolated monoclonal antibody, or the antigen-binding portion thereof, according to claim 1, which (a) binds human PD-L1; (b) binds monkey PD-L1; (c) does not bind to mouse PD-L1; (d) blocks PD-L1-PD-1 interaction; (e) promotes T cell activation; and (f) has an in vivo anti-tumor activity.

7. The isolated monoclonal antibody, or the antigen-binding portion thereof, according to claim 1, which is mouse, chimeric or humanized.

8. A nucleic acid molecule encoding the isolated monoclonal antibody, or antigen-binding portion thereof, according to claim 1.

9. An expression vector comprising the nucleic acid molecule according to claim 8.

10. A host cell comprising the expression vector according to claim 9.

11. A pharmaceutical composition comprising the isolated monoclonal antibody, or antigen-binding portion thereof, according to claim 1, and a pharmaceutically acceptable carrier.

12. A method for treating a cancer in a subject in need thereof, comprising administering to the subject the pharmaceutical composition according to claim 11.

13. The method according to claim 12, wherein the cancer is selected from the group consisting of melanoma, non-small cell lung cancer, renal cell carcinoma, Hodgkin lymphoma, bladder cancer, head and neck cancer, neuroendocrine tumor, mantle cell lymphoma, diffuse large B-cell lymphoma, and follicular lymphoma.

14. A method for treating an infectious disease in a subject in need thereof, comprising administering to the subject the pharmaceutical composition according to claim 11.

15. The method according to claim 14, wherein the infectious disease is chronic hepatitis B virus (HBV), hepatitis C virus (HCV), human immunodeficiency virus (HIV), or simian immunodeficiency virus (SIV) infection.

* * * * *